US009273026B2

(12) United States Patent
Auberson et al.

(10) Patent No.: US 9,273,026 B2
(45) Date of Patent: *Mar. 1, 2016

(54) CARBAMATE/UREA DERIVATIVES

(71) Applicants: Yves Auberson, Allscwil (CH); Mark Gary Bock, Boston, MA (US); Dario Braga, Casalecchio di Reno (IT); Marco Curzi, Bologna (IT); Stephanie Kay Dodd, Ayer, MA (US); Stefano Luca Giaffreda, Bologna (IT); Hayang Jiang, Shanghai (CN); Piotr Karpinski, Lincoln Park, MA (US); Thomas J. Troxler, Wahlen b. Laufen (CH); Tie-Lin Wang, Shanghai (CN); Xiaoyang Wang, Shanghai (CN); Xuechun Zhang, Guilford (CN)

(72) Inventors: Yves Auberson, Allscwil (CH); Mark Gary Bock, Boston, MA (US); Dario Braga, Casalecchio di Reno (IT); Marco Curzi, Bologna (IT); Stephanie Kay Dodd, Ayer, MA (US); Stefano Luca Giaffreda, Bologna (IT); Hayang Jiang, Shanghai (CN); Piotr Karpinski, Lincoln Park, MA (US); Thomas J. Troxler, Wahlen b. Laufen (CH); Tie-Lin Wang, Shanghai (CN); Xiaoyang Wang, Shanghai (CN); Xuechun Zhang, Guilford (CN)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/685,926

(22) Filed: Apr. 14, 2015

(65) Prior Publication Data
US 2015/0218127 A1 Aug. 6, 2015

Related U.S. Application Data

(63) Continuation of application No. 13/944,354, filed on Jul. 17, 2013, now Pat. No. 9,034,874.

(30) Foreign Application Priority Data

Jul. 20, 2012 (WO) ................ PCT/CN2012/078933
Jun. 28, 2013 (WO) ................ PCT/CN2013/078309

(51) Int. Cl.
A61K 31/501 (2006.01)
C07D 401/04 (2006.01)
A61K 31/496 (2006.01)
C07C 57/15 (2006.01)
C07C 59/265 (2006.01)
C07D 403/04 (2006.01)

(52) U.S. Cl.
CPC ............ *C07D 401/04* (2013.01); *A61K 31/496* (2013.01); *A61K 31/501* (2013.01); *C07C 57/15* (2013.01); *C07C 59/265* (2013.01); *C07D 403/04* (2013.01)

(58) Field of Classification Search
None
See application file for complete search history.

(56) References Cited

U.S. PATENT DOCUMENTS

| 4,613,603 A | 9/1986 | Biziere et al. |
| 2007/0049571 A1 | 3/2007 | Xie et al. |
| 2014/0163036 A1 | 6/2014 | Auberson et al. |

FOREIGN PATENT DOCUMENTS

| CN | 1993355 | 7/2007 |
| EP | 0169139 A1 | 1/1986 |
| EP | 0614664 A1 | 9/1994 |
| EP | 1717230 | 11/2006 |
| EP | 1970373 A1 | 9/2008 |
| EP | 2527340 A1 | 11/2012 |
| WO | 02/072570 A2 | 9/2002 |
| WO | 2004/101546 A1 | 11/2004 |
| WO | 2006/014136 A1 | 2/2006 |
| WO | 2006/029057 A1 | 3/2006 |
| WO | 2007/016496 A2 | 2/2007 |
| WO | 2007/052124 A1 | 5/2007 |
| WO | 2009/142732 | 11/2009 |
| WO | 2011/090062 A1 | 7/2011 |

OTHER PUBLICATIONS

Schwartz, Jean-Charles. "Review: The histatmine H3 receptor: from discovery to clinical trials with pitolisant." British Journal of Pharmacology. Jan. 2011, 163, pp. 713-721.
Barrett et al., Novel, potent P2-P3 pyrrolidine derivatives of ketoamide-based cathepsin K inihibitors, Bioorganic & Medicinal Chemistry Letters, vol. 16, No. 6, pp. 1735-1739 (2006).
Dandu et al., Synthesis and evaluation of pyridazinone-phenethylamine derivatives . . . , Bioorganic & Medicinal Chemistry Letters, vol. 21(21), pp. 6362-6365, (2011).
Database Registry Chemical Abstracts Service, XP002692465 (2011).
Lazewska et al., Recent advances in histamine H3 receptor antagonists/inverse agonists, Expert Opinion on Therapeutic Patents, vol. 20, No. 9, pp. 1147-1169, (2010).
Lin et al., Histamine H3 Receptors and Sleep-Wake Regulation, The Journal of Pharmacology and Experimental Therapeutics, JPET Miniseries: H3 Receptors, vol. 336, No. 1, (2011), pp. 17-23.
Raddatz et al., Histamine H3 Antagonists for Treatment of Cognitive Deficits in CNS Diseases, Current Topics in Medicinal Chemistry, vol. 10, pp. 153-169 (2010).

(Continued)

*Primary Examiner* — Emily Bernhardt
(74) *Attorney, Agent, or Firm* — Shawn D. Britt

(57) ABSTRACT

The invention relates to compound of the formula I (I)

or a salt thereof, wherein the substituents are as defined in the specification; to its preparation, to its use as medicament and to medicaments comprising it.

24 Claims, 9 Drawing Sheets

(56) References Cited

OTHER PUBLICATIONS

Sundar et al., Amine-constrained pyridazinone histamine H3 receptor antagonists, Bioorganic & Medicinal Chemistry Letters, vol. 21(18), pp. 5543-5546, (2011).

Vippagunta et al., Advanced Drug Delivery Reviews, vol. 48, pp. 3-26 (2001).
Phillips et al., Annual Reports in medicinal Chemistry, vol. 33, pp. 31-40 (1998).
Passani et al., Neuroscience and Biobehavioral Reviews, vol. 24, pp. 107-113 (2000).
Leurs et al., Trends in Pharmacol. Sci. 19(5), pp. 177-183 (1998).

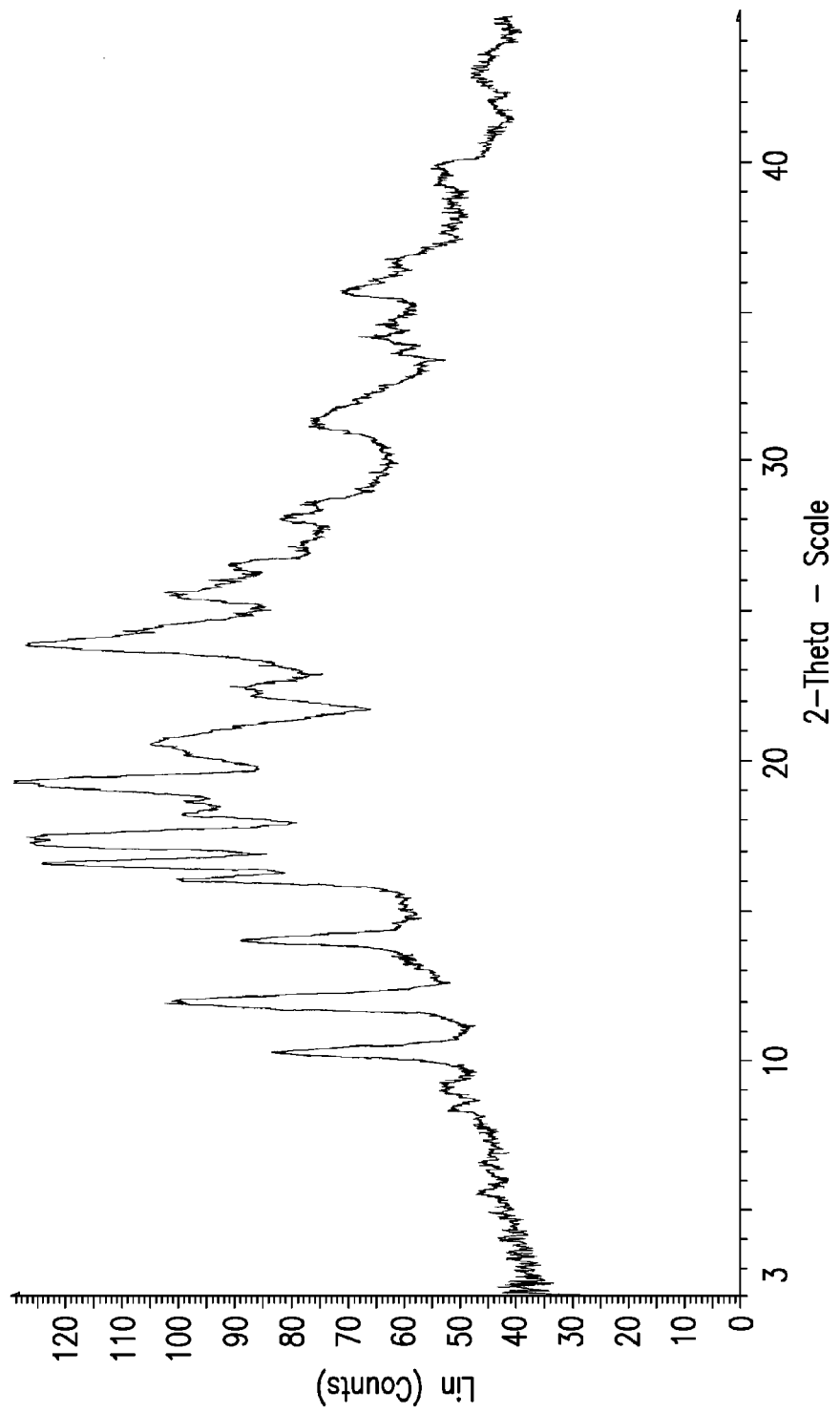

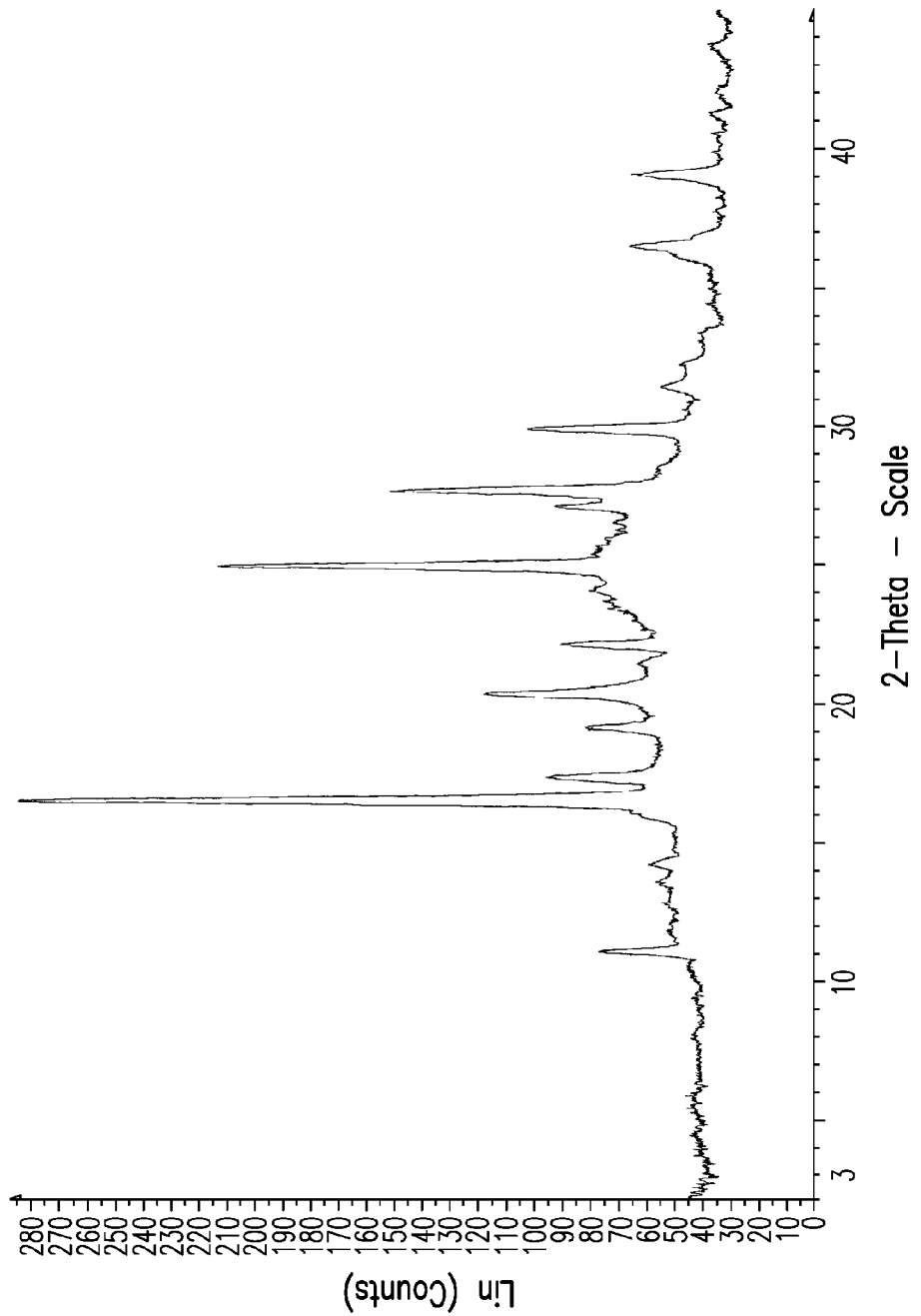

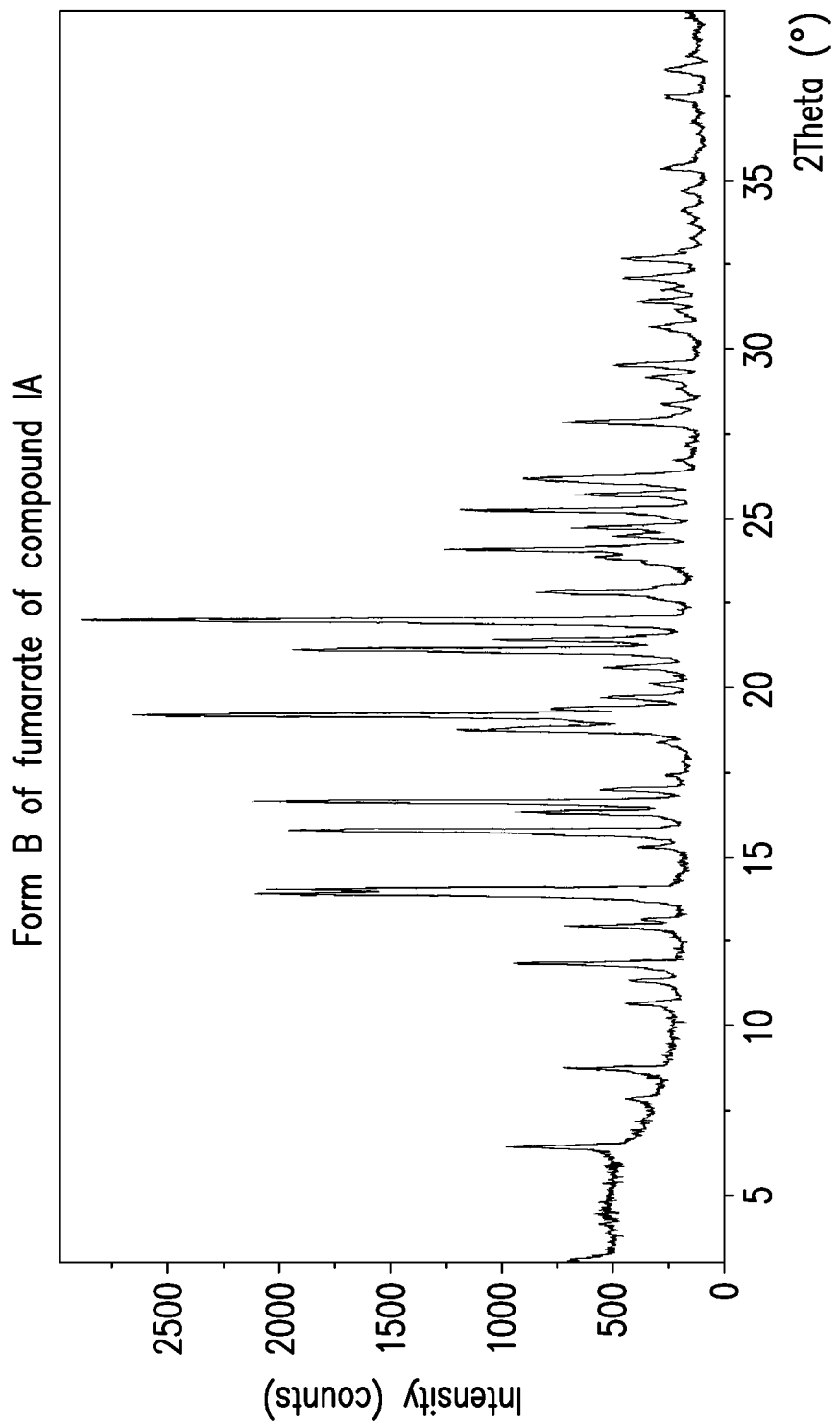

CARBAMATE/UREA DERIVATIVES

The invention relates to carbamate/urea derivatives, to their solid forms, to their preparation, to their use as medicaments and to medicaments comprising them.

I. Carbamate/Urea Derivatives

Histamine is a multifunctional chemical transmitter that signals through specific cell surface G-protein-coupled receptors (GPCRs). To date, four histamine receptors subtypes have been identified: H1, H2, H3 and H4. The H3 receptor is a presynaptic GPCR that is found predominantly in the central nervous system, although lower levels are also found in the peripheral nervous system. Genes encoding the H3 receptor have been reported in various organisms, including humans, and alternative splicing of this gene appears to result in multiple isoforms. The H3 receptor is an auto- and heteroreceptor whose activation leads to a decreased release of neurotransmitters (including histamine, acetylcholine, norepinephrine, dopamine and glutamate) from neurons in the brain, and is involved in the regulation of processes such as sleep and wakefulness, feeding and memory. In certain systems, the H3 receptor may be constitutively active.

Antagonists of H3 receptor increase release of cerebral histamine and other neurotransmitters, which in turn induces an extended wakefulness, an improvement in cognitive processes, a reduction in food intake and a normalization of vestibular reflexes. H3 receptor antagonists are described e.g. in Lazewska and Kiec-Kononowicz, Expert Opin Ther Patents, 2010, 20(9), 1147-1169; Raddatz et al, Current Topics in Medicinal Chemistry, 2010, 10, 153-169; WO2007052124; WO2007016496 and WO2004101546.

As histamine pathways have been implicated in a wide range of disorders, in particular disorders of sleep and wakefulness with excessive daytime sleepiness, e.g. narcolepsy, H3 receptor antagonists are considered to be useful for pharmacotherapy of said disorders.

There is a need to provide new H3 receptor antagonists that are good drug candidates. In particular, preferred compounds should bind potently to H3 receptors whilst showing little affinity for other receptors, e.g. receptors mediating significant side-effects, such as hERG channels which may induce cardiovascular side-effects. They should be well absorbed from the gastrointestinal tract, be sufficiently metabolically stable, possess favorable pharmacokinetic properties, sufficient brain uptake, fast onset and sufficiently long duration of action. For e.g. narcolepsy treatment, the pharmacokinetic property of the compound should lead to good wakefulness during daytime, but should equally lead to a minimal impact on night-sleep. The drug candidates should be non-toxic and demonstrate few side-effects. Furthermore, the ideal drug candidate will be able to exist in a physical form that is stable, non-hygroscopic and easily formulated.

The compounds of the invention are H3 receptor antagonists and are therefore potentially useful in the treatment of a wide range of disorders, particularly narcolepsy.

In a first aspect, the invention relates to a compound of the formula I

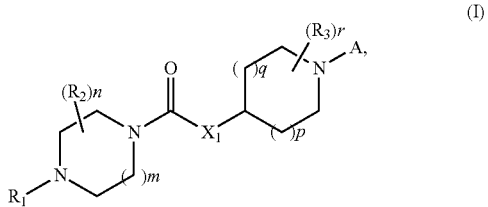

(I)

or a salt thereof, wherein $R_1$ is $C_{1-6}$alkyl, $C_{2-6}$alkenyl, $C_{2-6}$alkinyl, $C_{3-6}$cycloalkyl, $C_{5-6}$cycloalkenyl or $C_{3-6}$cycloalkyl-$C_{1-4}$alkyl; wherein said $C_{1-6}$alkyl, $C_{2-6}$alkenyl, $C_{2-6}$alkinyl or $C_{3-6}$cycloalkyl-$C_{1-4}$alkyl may be substituted once or more than once by halogen; and wherein said $C_{3-6}$cycloalkyl or $C_{5-6}$cycloalkenyl may be substituted once or more than once by halogen, $C_{1-4}$alkyl or $C_{1-4}$halogenalkyl;

m is 1 or 2;

n is 0, 1, 2, 3 or 4;

each $R_2$ independently is halogen, hydroxyl, amino, cyano, nitro, $C_{1-6}$alkyl, $C_{1-6}$halogenalkyl, $C_{1-6}$hydroxyalkyl, $C_{1-4}$alkoxy-$C_{1-6}$alkyl, amino-$C_{1-6}$alkyl, $C_{1-4}$alkyl-amino-$C_{1-6}$alkyl, di($C_{1-4}$alkyl)amino-$C_{1-6}$alkyl, $C_{1-6}$alkoxy, $C_{1-6}$halogenalkoxy, $C_{1-6}$alkylamino, di($C_{1-6}$alkyl)amino, $C_{2-6}$alkenyl, $C_{2-6}$halogenalkenyl, $C_{2-6}$alkinyl or $C_{2-6}$halogenalkinyl;

or $C_{3-6}$cycloalkyl, wherein one carbon atom may be replaced by an oxygen atom, wherein the $C_{3-6}$cycloalkyl may be attached directly to the methylene or via a $C_{1-2}$alkylene, and wherein the $C_{3-6}$cycloalkyl may be substituted once or more than once by halogen;

or two $R_2$ at the same carbon atom form together with said carbon atom a $C_{3-6}$cycloalkyl;

$X_1$ is oxygen or —N($R_4$)—;

$R_4$ is hydrogen, $C_{1-6}$alkyl, $C_{3-6}$cycloalkyl, or $C_{3-6}$cycloalkyl-$C_{1-2}$alkyl;

p is 1 and q is 1;

p is 0 and q is 1; or p is 0 and q is 0;

r is 0, 1, 2, 3 or 4;

each $R_3$ independently is halogen, hydroxyl, amino, cyano, nitro, $C_{1-6}$alkyl, $C_{1-6}$halogenalkyl, $C_{1-6}$hydroxyalkyl, $C_{1-4}$alkoxy-$C_{1-6}$alkyl, amino-$C_{1-6}$alkyl, $C_{1-4}$alkyl-amino-$C_{1-6}$alkyl, di($C_{1-4}$alkyl)amino-$C_{1-6}$alkyl, $C_{1-6}$alkoxy, $C_{1-6}$halogenalkoxy, $C_{1-6}$alkylamino, di($C_{1-6}$alkyl)amino, $C_{2-6}$alkenyl, $C_{2-6}$halogenalkenyl, $C_{2-6}$alkinyl or $C_{2-6}$halogenalkinyl;

or $C_{3-6}$cycloalkyl, wherein one carbon atom may be replaced by an oxygen atom, wherein the $C_{3-6}$cycloalkyl may be attached directly to the methylene or via a $C_{1-2}$alkylene, and wherein the $C_{3-6}$cycloalkyl may be substituted once or more than once by halogen;

or two $R_3$ at the same carbon atom form together with said carbon atom a $C_{3-6}$cycloalkyl;

A is

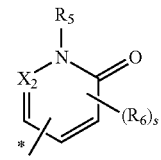

wherein the bond marked with the asterisk is attached to the nitrogen atom;

$R_5$ is hydrogen, $C_{1-6}$alkyl, $C_{2-6}$alkenyl, $C_{2-6}$alkinyl, $C_{3-6}$cycloalkyl, $C_{5-6}$cycloalkenyl or $C_{3-6}$cycloalkyl-$C_{1-4}$alkyl; wherein said $C_{1-6}$alkyl, $C_{2-6}$alkenyl, $C_{2-6}$alkinyl or $C_{3-6}$cycloalkyl-$C_{1-4}$alkyl may be substituted once or more than once by halogen, hydroxyl or $C_{1-6}$alkoxy; and wherein said $C_{3-6}$cycloalkyl or $C_{5-6}$cycloalkenyl may be substituted once or more than once by halogen, $C_{1-4}$alkyl or $C_{1-4}$halogenalkyl;

$X_2$ is nitrogen or carbon;

s is 0, 1, 2 or 3;

each $R_6$ independently is halogen, hydroxyl, amino, cyano, nitro, $C_{1-6}$alkyl, $C_{1-6}$halogenalkyl, $C_{1-6}$hydroxyalkyl, $C_{1-4}$alkoxy-$C_{1-6}$alkyl, amino-$C_{1-6}$alkyl, $C_{1-4}$alkyl-amino-$C_{1-6}$alkyl, di($C_{1-4}$alkyl)amino-$C_{1-6}$alkyl, $C_{1-6}$alkoxy, $C_{1-6}$halogenalkoxy, $C_{1-6}$alkylamino, di($C_{1-6}$alkyl)amino, $C_{2-6}$alkenyl, $C_{2-6}$halogenalkenyl, $C_{2-6}$alkinyl or $C_{2-6}$halogenalkinyl;

or $C_{3-6}$cycloalkyl, wherein one carbon atom may be replaced by an oxygen atom, wherein the $C_{3-6}$cycloalkyl may be attached directly to the methylene or via a $C_{1-2}$alkylene, and wherein the $C_{3-6}$cycloalkyl may be substituted once or more than once by halogen.

Unless specified otherwise, the term "compounds of the invention" refers to compounds of formula (I) and subformulae thereof (e.g. compounds of formula (I-1)); prodrugs thereof; solid forms of free forms or salts of the compounds, e.g. SOLID FORMS OF THE INVENTION, and/or prodrugs; hydrates or solvates of the compounds, salts and/or prodrugs; as well as all stereoisomers (including diastereoisomers and enantiomers), tautomers and isotopically labeled compounds (including deuterium substitutions); as well as inherently formed moieties (e.g. polymorphs, solvates and/or hydrates).

Unless indicated otherwise, the expressions used in this invention have the following meaning:

"Alkyl" represents a straight-chain or branched-chain alkyl group and, for example, may be methyl, ethyl, n- or iso-propyl, n-, iso-, sec- or tert-butyl, n-pentyl, n-hexyl; $C_{1-6}$alkyl preferably represents a straight-chain or branched-chain $C_{1-4}$alkyl with particular preference given to methyl, ethyl, n-propyl, iso-propyl and tert-butyl.

Each alkyl part of "alkoxy", "halogenalkyl" and so on shall have the same meaning as described in the above-mentioned definition of "alkyl", especially regarding linearity and preferential size.

"$C_{3-6}$cycloalkyl" represents a saturated alicyclic moiety having from three to six carbon atoms. This term refers to groups such as cyclopropyl, cyclobutyl, cyclopentyl and cyclohexyl.

A substituent being substituted "once or more than once", e.g. as defined in connection with $R_1$, is preferably substituted by one to three substituents.

Halogen is generally fluorine, chlorine, bromine or iodine; preferably fluorine, chlorine or bromine. Halogenalkyl groups preferably have a chain length of 1 to 4 carbon atoms and are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,2-trichloroethyl, 1,1,2,2-tetrafluoroethyl, 2,2,3,3-tetrafluoropropyl, 2,2,3,3,3-pentafluoropropyl or 2,2,3,4,4,4-hexafluorobutyl.

In the event $X_2$ being carbon, said carbon can be unsubstituted, substituted by a $R_6$ or used to attach A to the nitrogen of the neighbouring piperidine/pyrrolidine/azetidine moiety.

Compounds of formula I may exist in optically active form or in form of mixtures of optical isomers, e.g. in form of racemic mixtures or diastereomeric mixtures. In particular, asymmetrical carbon atom(s) may be present in the compounds of formula I and their salts. Unless otherwise provided herein, all optical isomers and their mixtures, including the racemic mixtures, are embraced by the invention.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. The compounds described herein may contain one or more asymmetric centers and may thus give rise to enantiomers, diastereomers, and other stereoisomeric forms that may be defined, in terms of absolute stereochemistry, as (R)- or (S)-. Unless otherwise provided herein, the invention is meant to include all such possible isomers, including racemic mixtures, optically pure forms and intermediate mixtures. Optically active (R)- and (S)-isomers may be prepared using chiral synthons or chiral reagents, or resolved using conventional techniques.

If the compound contains a double bond, the substituent may be E or Z configuration.

If the compound contains a disubstituted cycloalkyl, the cycloalkyl substituent may have a cis- or trans-configuration.

Any asymmetric atom (e.g. carbon or the like) of the compound(s) of the invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein, a compound of the invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Depending on substituent definition, compounds of formula I may occur in various tautomeric forms. All tautomeric forms of the compounds of formula I are embraced by the invention.

As used herein, the terms "salt" or "salts" refers to an acid addition or base addition salt of a respective compound, e.g. a compound of the invention or of a compound of formula II-1. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. The compounds of the invention may be capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

When both a basic group and an acid group are present in the same molecule, the compounds of the invention may also form internal salts, e.g., zwitterionic molecules.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula I with the co-crystal former under crystallization conditions and isolating co-crystals thereby formed. Suitable co-crystal formers include those described in WO 2004/078163. Hence the invention further provides co-crystals comprising a compound of formula (I).

The invention also provides pro-drugs of the compounds of the invention that convert in vivo to the compounds of the invention. A pro-drug is an active or inactive compound that is modified chemically through in vivo physiological action, such as hydrolysis, metabolism and the like, into a compound of the invention following administration of the prodrug to a subject. The suitability and techniques involved in making and using pro-drugs are well known by those skilled in the art. See The Practice of Medicinal Chemistry, Ch. 31-32 (Ed. Wermuth, Academic Press, San Diego, Calif., 2001).

Furthermore, the compounds of the invention, including their salts, can also be obtained in the form of their hydrates, or include other solvents used for their crystallization. The compounds of the invention may inherently or by design form solvates with pharmaceutically acceptable solvents (including water); therefore, it is intended that the invention embrace both solvated and unsolvated forms. The term "solvate" refers to a molecular complex of a compound of the invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the invention, including salts, hydrates and solvates thereof, may inherently or by design form polymorphs.

Preferred substituents, preferred ranges of numerical values or preferred ranges of the radicals present in compounds of the formula I and the corresponding intermediate compounds are defined below. The definition of the substituents applies to the end-products as well as to the corresponding intermediates. The definitions of the substituents may be combined at will, e.g. preferred substituents A and particularly preferred substituents $R_1$.

In one embodiment, the invention provides a compound of formula I, wherein $R_1$ is $C_{1-6}$alkyl, $C_{3-6}$cycloalkyl, $C_{3-6}$cycloalkyl-$C_{1-2}$alkyl.

In one embodiment, the invention provides a compound of formula I, wherein $R_1$ is $C_{3-4}$alkyl or $C_{3-5}$cycloalkyl.

In one embodiment, the invention provides a compound of formula I, wherein $R_1$ is isopropyl, cyclopropyl, cyclobutyl or cyclopentyl.

In one embodiment, the invention provides a compound of formula I, wherein $R_1$ is isopropyl.

In one embodiment, the invention provides a compound of formula I, wherein $R_1$ is cyclobutyl.

In one embodiment, the invention provides a compound of formula I, wherein m is 1.

In one embodiment, the invention provides a compound of formula I, wherein m is 2.

In one embodiment, the invention provides a compound of formula I, wherein n is 0, 1 or 2 and wherein each $R_2$ independently is halogen, $C_{1-4}$alkyl, $C_{1-4}$halogenalkyl, $C_{1-4}$alkoxy, $C_{1-4}$halogenalkoxy or $C_{3-4}$cycloalkyl; or two $R_2$ at the same carbon atom form together with said carbon atom a $C_{3-4}$cycloalkyl.

In one embodiment, the invention provides a compound of formula I, wherein n is 0.

In one embodiment, the invention provides a compound of formula I, wherein $X_1$ is oxygen.

In one embodiment, the invention provides a compound of formula I, wherein $X_1$ is —N($R_4$)— and $R_4$ is hydrogen, $C_{1-6}$alkyl, $C_{3-6}$cycloalkyl, or $C_{3-6}$cycloalkyl-$C_{1-2}$alkyl.

In one embodiment, the invention provides a compound of formula I, wherein $X_1$ is —N($R_4$)— and $R_4$ is hydrogen.

In one embodiment, the invention provides a compound of formula I, wherein p is 1 and q is 1.

In one embodiment, the invention provides a compound of formula I, wherein p is 0 and q is 1.

In one embodiment, the invention provides a compound of formula I, wherein p is 0 and q is 0.

In one embodiment, the invention provides a compound of formula I, wherein r is 0, 1 or 2 and wherein each $R_3$ independently is halogen, $C_{1-4}$alkyl, $C_{1-4}$halogenalkyl, $C_{1-4}$alkoxy, $C_{1-4}$halogenalkoxy or $C_{3-4}$cycloalkyl; or two $R_3$ at the same carbon atom form together with said carbon atom a $C_{3-4}$cycloalkyl.

In one embodiment, the invention provides a compound of formula I, wherein r is 0.

In one embodiment, the invention provides a compound of formula I, wherein A is A1

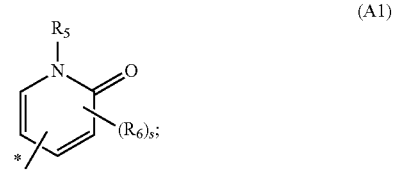

(A1)

wherein the bond marked with the asterisk is attached to the nitrogen atom.

In one embodiment, the invention provides a compound of formula I, wherein A is A1;
$R_5$ is hydrogen, $C_{1-4}$alkyl, $C_{1-4}$halogenalkyl or $C_{3-4}$cycloalkyl;
s is 0, 1 or 2; and
each $R_6$ independently is halogen, $C_{1-4}$alkyl, $C_{1-4}$halogenalkyl, $C_{1-4}$alkoxy, $C_{1-4}$halogenalkoxy or $C_{3-4}$cycloalkyl.

In one embodiment, the invention provides a compound of formula I, wherein A is A1, $R_5$ is hydrogen or methyl, and s is 0.

In one embodiment, the invention provides a compound of formula I, wherein A is A2

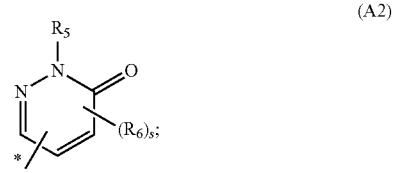

(A2)

wherein the bond marked with the asterisk is attached to the nitrogen atom;
and s is 0, 1 or 2.

In one embodiment, the invention provides a compound of formula I, wherein A is A2;
$R_5$ is hydrogen, $C_{1-4}$alkyl, $C_{1-4}$halogenalkyl or $C_{3-4}$cycloalkyl;
s is 0, 1 or 2; and each $R_6$ independently is halogen, $C_{1-4}$alkyl, $C_{1-4}$halogenalkyl, $C_{1-4}$alkoxy, $C_{1-4}$halogenalkoxy or $C_{3-4}$cycloalkyl.

In one embodiment, the invention provides a compound of formula I, wherein A is A2, $R_5$ is hydrogen or methyl, and s is 0.

In one embodiment, the invention provides a compound of formula I, wherein A is A3

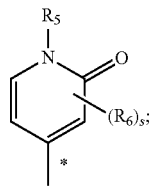

(A3)

wherein the bond marked with the asterisk is attached to the nitrogen atom.

In one embodiment, the invention provides a compound of formula I, wherein A is A3;
$R_5$ is hydrogen, $C_{1-4}$alkyl, $C_{1-4}$halogenalkyl or $C_{3-4}$cycloalkyl;
s is 0, 1 or 2; and
each $R_6$ independently is halogen, $C_{1-4}$alkyl, $C_{1-4}$halogenalkyl, $C_{1-4}$alkoxy, $C_{1-4}$halogenalkoxy or $C_{3-4}$cycloalkyl.

In one embodiment, the invention provides a compound of formula I, wherein A is A3, $R_5$ is hydrogen or methyl, and s is 0.

In one embodiment, the invention provides a compound of formula I, wherein A is A4

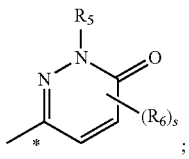

(A4)

wherein the bond marked with the asterisk is attached to the nitrogen atom;
and s is 0, 1 or 2.

In one embodiment, the invention provides a compound of formula I, wherein A is A4;
$R_5$ is hydrogen, $C_{1-4}$alkyl, $C_{1-4}$halogenalkyl or $C_{3-4}$cycloalkyl;
s is 0, 1 or 2; and
each $R_6$ independently is halogen, $C_{1-4}$alkyl, $C_{1-4}$halogenalkyl, $C_{1-4}$alkoxy, $C_{1-4}$halogenalkoxy or $C_{3-4}$cycloalkyl.

In one embodiment, the invention provides a compound of formula I, wherein A is A4, $R_5$ is hydrogen or methyl, and s is 0.

In one embodiment, the invention provides a compound of formula I, wherein
$R_1$ is isopropyl or cyclobutyl; m is 1; n is 0, 1 or 2; each $R_2$ independently is halogen, $C_{1-4}$alkyl, $C_{1-4}$halogenalkyl, $C_{1-4}$alkoxy, $C_{1-4}$halogenalkoxy or $C_{3-4}$cycloalkyl; or two $R_2$ at the same carbon atom form together with said carbon atom a $C_{3-4}$cycloalkyl;
$X_1$ is oxygen;
p is 1 and q is 1; r is 0, 1 or 2; wherein each $R_3$ independently is halogen, $C_{1-4}$alkyl, $C_{1-4}$halogenalkyl, $C_{1-4}$alkoxy, $C_{1-4}$halogenalkoxy or $C_{3-4}$cycloalkyl; or two $R_3$ at the same carbon atom form together with said carbon atom a $C_{3-4}$cycloalkyl; A is selected from A3 and A4

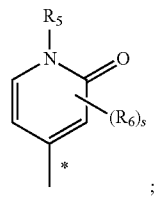

(A3)

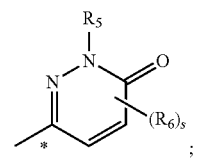

(A4)

wherein the bond marked with the asterisk is attached to the nitrogen atom;
$R_5$ is hydrogen or methyl;
s is 0, 1 or 2; and
each $R_6$ independently is halogen, $C_{1-4}$alkyl, $C_{1-4}$halogenalkyl, $C_{1-4}$alkoxy, $C_{1-4}$halogenalkoxy or $C_{3-4}$cycloalkyl.

In one embodiment, the invention provides a compound of formula I, wherein
$R_1$ is isopropyl or cyclobutyl; m is 1 and n is 0;
$X_1$ is oxygen;
p is 1 and q is 1; r is 0; and A is
is selected from A3 and A4

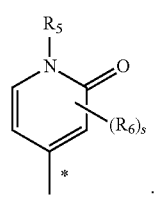

(A3)

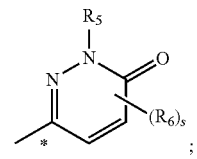

(A4)

wherein the bond marked with the asterisk is attached to the nitrogen atom;
and $R_5$ is hydrogen or methyl; and s is 0.

In one embodiment, the invention provides a compound of formula I, wherein
$R_1$ is $C_{1-6}$alkyl or $C_{3-6}$cycloalkyl;
m is 1 and n is 0;
$X_1$ is oxygen;
p is 1 and q is 1; r is 0; and A is

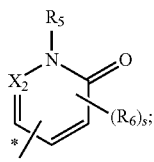

wherein the bond marked with the asterisk is attached to the nitrogen atom;

$X_2$ is nitrogen or carbon;

$R_5$ is hydrogen or $C_{1-6}$alkyl; and s is 0.

In one embodiment, the invention provides a compound of formula I, wherein $R_1$ is $C_{1-6}$alkyl or $C_{3-6}$cycloalkyl;

m is 1 and n is 0;

$X_1$ is oxygen;

p is 1 and q is 1; r is 0; and

A is selected from A3 and A4

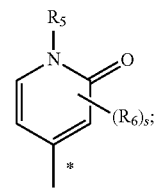 (A3)

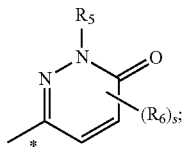 (A4)

wherein the bond marked with the asterisk is attached to the nitrogen atom;

$X_2$ is nitrogen or carbon;

$R_5$ is hydrogen, methyl or ethyl; and s is 0.

In one embodiment, the invention provides a compound of formula I, wherein $R_1$ is isopropyl, cyclopropyl or cyclobutyl;

m is 1 and n is 0;

$X_1$ is oxgen;

p is 1 and q is 1; r is 0; and A is is selected from A3 and A4

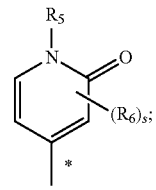 (A3)

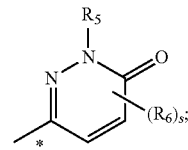 (A4)

wherein the bond marked with the asterisk is attached to the nitrogen atom;

$R_5$ is hydrogen, methyl or ethyl; and s is 0.

In preferred embodiments, the invention relates to one or more than one of the compounds of the formula I mentioned in the Examples hereinafter or to a salt thereof.

Further examples of suitable compounds of the invention are compounds selected from the following group P:

Group P: Suitable Compounds of the Invention:

1-(6-oxo-1,6-dihydropyridazin-3-yl)piperidin-4-yl 4-cyclobutylpiperazine-1-carboxylate;

1-(1-methyl-6-oxo-1,6-dihydropyridazin-3-yl)piperidin-4-yl 4-isopropylpiperazine-1-carboxylate;

1-(6-oxo-1,6-dihydropyridazin-3-yl)piperidin-4-yl 4-isopropylpiperazine-1-carboxylate;

1-(6-oxo-1,6-dihydropyridazin-3-yl)piperidin-4-yl 4-cyclopropylpiperazine-1-carboxylate;

1-(1-methyl-6-oxo-1,6-dihydropyridazin-3-yl)piperidin-4-yl 4-cyclobutylpiperazine-1-carboxylate;

1-(1-ethyl-6-oxo-1,6-dihydropyridazin-3-yl)piperidin-4-yl 4-isopropylpiperazine-1-carboxylate;

1-(1-methyl-2-oxo-1,2-dihydropyridin-4-yl)piperidin-4-yl 4-isopropylpiperazine-1-carboxylate;

1-(2-oxo-1,2-dihydropyridin-4-yl)piperidin-4-yl 4-cyclobutylpiperazine-1-carboxylate;

1-(2-oxo-1,2-dihydropyridin-4-yl)piperidin-4-yl 4-isopropylpiperazine-1-carboxylate; or 1-(6-oxo-1,6-dihydropyridin-3-yl)piperidin-4-yl 4-isopropylpiperazine-1-carboxylate;

or salts of these compounds.

In a further aspect, the invention also provides a process for the production of compounds of the formula I-1. Compounds of the formula I-1 are obtainable according to the following process as described in scheme 1:

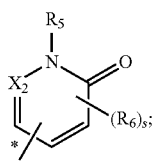

Scheme 1:

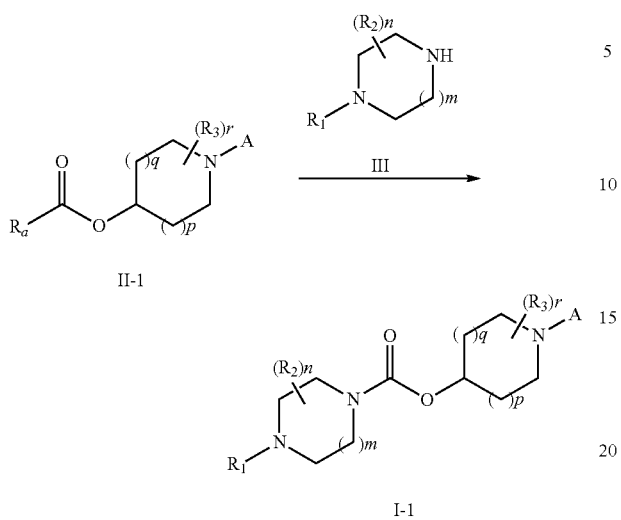

A compound of formula I-1, in which A, $R_1$, $R_2$, $R_3$, m, n, p, q and r are as defined under formula I, may be obtained by reacting a compound of formula II-1, in which A, $R_3$, p, q and r are as defined under formula I and $R_a$ is a leaving group, e.g. halogen, such as chloro, or 4-nitrophenyloxy (preferably $R_a$ is 4-nitrophenyloxy), with a compound of formula III, in which $R_1$, $R_2$, m and n are as defined under formula I, in the presence of a suitable base, e.g. diisopropylethylamine, in the presence of a suitable solvent, e.g. pyridine.

In a further aspect, the invention also provides a process for the production of compounds of the formula I-2. Compounds of the formula I-2 are obtainable according to the following process as described in scheme 2:

Scheme 2:

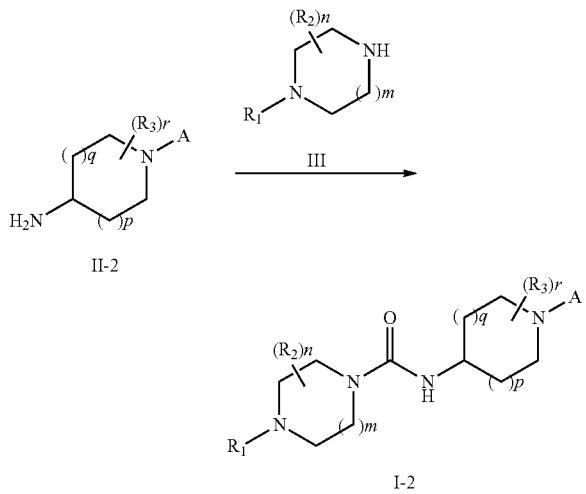

A compound of formula I-2, in which A, $R_1$, $R_2$, $R_3$, m, n, p, q and r are as defined under formula I, may be obtained by reacting a compound of formula II-2, in which A, $R_3$, p, q and r are as defined under formula I, with a compound of formula III, in which in which $R_1$, $R_2$, m and n are as defined under formula I, in the presence of carbonyldiimidazole, a suitable base, e.g. diisopropylethylamine, and a suitable solvent, e.g. dimethylformamide.

Further compounds of formula I or their precursors may be obtainable from compounds of formula I-1 or I-2, prepared as described according to scheme 1 or 2, or their precursors (e.g. compounds of formulae II-1, II-2 and/or III) by reduction, oxidation and/or other functionalization of resulting compounds and/or by cleavage of any protecting group(s) optionally present, and of recovering the so obtainable compound of the formula I. Compounds of the formula I can also be prepared by further conventional processes, e.g. as described in the Examples, which processes are further aspects of the invention.

The invention also contemplates that compounds of formula (I) may be formed by in vivo biotransformation from pro-drugs.

The reactions can be effected according to conventional methods, for example as described in the Examples.

The work-up of the reaction mixtures and the purification of the compounds thus obtainable may be carried out in accordance with known procedures.

Acid addition salts may be produced from the free bases in known manner, and vice-versa.

Starting materials, e.g. compounds of the formulae II-1, II-2 and III may be known or prepared according to conventional procedures starting from known compounds, for example as described in the Examples.

In a further aspect, the invention also provides a process for the production of compounds of the formula II-1. Compounds of the formula II-1 are obtainable according to the following process as described in scheme 3:

Scheme 3:

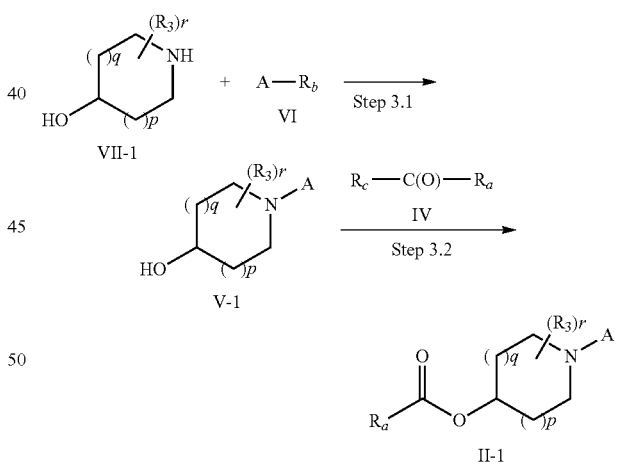

Step 3.1:
A compound of formula V-1, in which A, $R_3$, p, q and r are as defined under formula I, may be obtained by reacting a compound of formula VII-1, in which $R_3$, p, q and r are as defined under formula I, with a compound of formula VI, in which A is as defined under formula I and $R_b$ is halogen, for example chloro, in the presence of a suitable base, e.g. diisopropylethylamine, and optionally in the presence of a suitable solvent.

Step 3.2:
A compound of formula II-1, in which A, $R_1$, $R_2$, $R_3$, m, n, p, q and r are as defined under formula I, may be obtained by reacting the compound of V-1 with a compound of formula IV, in which $R_c$ is halogen, for example chloro, and $R_a$ is a leaving group, e.g. halogen or 4-nitrophenyloxy (preferably $R_a$ is 4-nitrophenyloxy), in the presence of a suitable base, e.g. diisopropylethylamine, and in the presence of a suitable solvent, e.g. pyridine.

In a further aspect, the invention also provides a novel compound of formula II-1

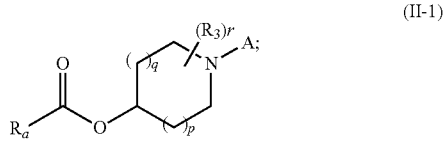

or a salt thereof; in which p, q, r, $R_3$ and A are as defined under formula I; $R_a$ is a leaving group, e.g. halogen, such as chloro, or a group selected from

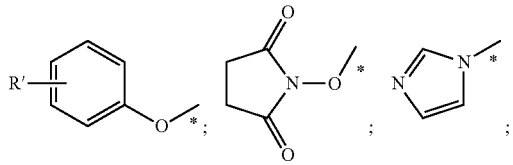

wherein the bond marked with the asterisk is attached to the carbonyl group;

wherein R' is hydrogen or nitro; preferably $R_a$ is 4-nitrophenyloxy.

In one embodiment of said further aspect, the invention provides a compound of formula II-1, wherein
p is 1 and q is 1;
p is 0 and q is 1; or
p is 0 and q is 0;
r is 0, 1 or 2 and wherein each $R_2$ independently is halogen, $C_{1-4}$alkyl, $C_{1-4}$halogenalkyl, $C_{1-4}$alkoxy, $C_{1-4}$halogenalkoxy or $C_{3-4}$cycloalkyl; or two $R_2$ at the same carbon atom form together with said carbon atom a $C_{3-4}$cycloalkyl; and
A is A4 or A5.

In one embodiment of said further aspect, the invention provides a compound of formula II-1, wherein $R_1$ is isopropyl; m is 1; $X_1$ is oxygen; p is 1 and q is 1; n is 0; p is 1 and q is 1; A is A4 or A5; and $R_5$ is hydrogen or methyl, In one embodiment of said further aspect, the invention provides a compound of formula II-1, wherein $R_1$ is cyclobutyl; m is 1; $X_1$ is oxygen; p is 1 and q is 1; n is 0; p is 1 and q is 1; A is A4 or A5; and $R_5$ is hydrogen or methyl, In another aspect, the invention provides a pharmaceutical composition comprising a compound of the invention and a pharmaceutically acceptable carrier. The pharmaceutical composition can be formulated for particular routes of administration such as oral administration, parenteral administration, and rectal administration, etc. In addition, the pharmaceutical compositions of the invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides anhydrous pharmaceutical compositions and dosage forms comprising the compounds of the invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the invention as an active ingredient will decompose. Such agents, which are referred to herein as "stabilizers," include, but are not limited to, antioxidants such as ascorbic acid, pH buffers, or salt buffers, etc.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The compounds of formula I or pharmaceutical acceptable salts thereof exhibit valuable pharmacological properties and are therefore useful as pharmaceuticals.

Furthermore, compounds of formula I may be useful for research on H3 receptors, e.g. as tool compounds.

In particular, compounds of formula I exhibit a H3 receptor antagonistic action at human H3 receptors.

As used herein, the term "H3 receptor antagonist" encompasses H3 receptor inverse agonists and H3 receptor neutral antagonists.

H3 receptor antagonistic action can be determined in vitro, for example, at recombinant human H3 receptors, using different procedures like, for example, measurement of the inhibition of the agonist induced elevation of intracellular cAMP concentration, e.g. as described herein.

The compounds of the invention may be therefore useful in the prevention, treatment or delay of progression of disorders mediated by H3 receptors.

Disorders mediated by H3 receptors may be for example i) disorders of sleep and wakefulness with excessive daytime sleepiness; such as narcolepsy, e.g. narcolepsy with or without cataplexy; secondary narcoleptic syndromes; central sleep apnea syndrome; or obstructive sleep apnea syndrome;

ii) disorders or conditions associated with increased fatigue or hypersomnolence; such as fatigue associted with autoimmune disease, e.g. Multiple Sclerosis or Rheumatoid Arthritis; fatigue associated with neurodegenerative disorders, e.g. as Parkinson's disease, Multisystem atrophy, Shy-Drager-Syndrome or Progressive Supranuclear Palsy; fatigue associated with other medical conditions or their treatment, such as depression, burnout syndrome, or adjustment disorder; stress-associated disorders with fatigue, e.g. acute stress disorder or posttraumatic stress disorder; cancer-associated fatigue; chemotherapy-associated fatigue; fatigue associated with shift-work; jet lag; chronic fatigue syndrome; fibromyalgia; postinfectious fatigue; postoperative fatigue or dizziness;

iii) disorders or conditions with impaired cognition; such as Alzheimers Disease; Mild Cognitive Impairment; Diffuse-Lewy body dementia; vascular dementia; Huntington's disease; Wilson's disease; frontotemporal dementia; other forms of organic dementia or organic cognitive impairment; multiple sclerosis; schizophenia; schizoaffective disorder; bipolar-affective disorder;

iv) disorders of substance abuse or addiction; such as to alcohol, cocaine, opioids, cannabinoids, nicotine or other substances with abuse or addiction potential;

v) non-substance abuse conditions; such as pathological gambling;

vi) disorders associated with dysfunctional feeding behaviours and/or metabolic syndrome; such as antipsychotic drug-associated weight gain; Prader-Willi-Sndrome; Moon-Bardet-Biedl Syndrome; obesity; atypical depression; bulimia nervosa; or binge eating disorder;

vii) disorders with increased anxiety; such as general anxiety disorder; social anxiety disorder; or panic disorder;

viii) other neuropsychiatric or neurological disorders; such as Tourette syndrome; primary tic disorders; secondary tic disorders; attention deficit hyperactivity disorders; obesessive-compulsive disorders; headache disorders, e.g. episodic migraine, chronic migraine, cluster headache, or tension-type headache; acute disordes associated with neuronal loss, e.g. stroke; REM-sleep behavioural disorder; restless-legs syndrome; or epilepsy;

ix) other medical conditions or disorders; such as disorders with impaired hearing; vertigo; Menieres Disease; itch; pruritus; inflammatory pain; neuropathic pain; diabetes mellitus; cancer; atherosclerosis; allergies; or allergic rhinitis;

Of particular importance is the treatment of narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; or Attention-deficit hyperactivity disorder.

For the above-mentioned indications (the conditions and disorders) the appropriate dosage will vary depending upon, for example, the compound employed, the host, the mode of administration and the nature and severity of the condition being treated. However, in general, satisfactory results in animals are indicated to be obtained at a daily dosage of from about 0.001 to about 500 mg/kg body weight, preferably from about 0.1 to about 10 mg/kg body weight, e.g. 1 mg/kg. In larger mammals, for example humans, an indicated daily dosage is in the range from about 0.1 to about 1000 mg, preferably from about 0.1 to about 400 mg, most preferably from about 0.1 to about 100 mg of the compound of the invention conveniently administered, for example, in divided doses up to four times a day.

For use according to the invention, a compound of the invention may be administered as single active agent or in combination with other active agents, in any usual manner, e.g. orally, for example in the form of tablets or capsules, or parenterally, for example in the form of injection solutions or suspensions. A combination comprising a compound of the invention and one or more other therapeutically active agents will be referred to as "combination of the invention".

In the case of narcolepsy, the compound of the invention may be combined at least with one active agent selected from the group consisting of a noradrenaline-dopamine reuptake inhibitor, such as modafinil or armodafinil;

a tri- or tetracyclic antidepressant, such as clomipramine;

a serotonin-noradrenaline reuptake inhibitor, such as venlafaxine or duloxetine;

a selective serotonin reuptake inhibitor, such as paroxetine;

a noradrenaline reuptake inhibitor, such as reboxetine or atomoxetine;

a MAO-B inhibitor such as selegiline;

a gamma-hydroxy-butyrate; and a psychostimulant, such as methylphenidate.

Said combination of the invention is useful to treat narcolepsy.

In the case of fatigue associated with multiple sclerosis, the compound of the invention may be combined at least with one active agent selected from the group consisting of a sphingosine-1-phosphate analog, such as fingolimod; and another immunosuppressive agent, such as prednisolone or methotrexate.

In the case of fatigue associated with Parkinson's disease, the compound of the invention may be combined at least with one active agent selected from the group consisting of L-Dopa with or without a Decarboxylase inhibitor, such as Benzerazid or Carbidopa, and/or with or without a catechol-O-Methytransferase inhibitor, such as entacapone or tolcapone;

a dopamine receptor agonist, such as ropinirole or pergolide; and a MAO-B inhibitor, such as selegiline.

In the case of cognitive impairment associated with schizophrenia, the compound of the invention may be combined at least with one antipsychotic agent, such as haloperidol, olanzapine; risperidone; quetiapine; amisulpiride; or aripirazole.

In the case of cognitive impairment associated with Alzheimer's disease, the compound of the invention may be combined at least with one active agent selected from the group consisting of a cholinergic agent, such as an acetylcholinesterase inhibitor, e.g. donepezil, rivastigmine or galantamine; and an antiglutamatergic agent, such as memantine, selfotel or midafotel.

In the case of cognitive impairment associated with Alzheimer's disease, the compound of the invention may be combined at least with one active agent selected from the group consisting of a cholinergic agent, such as an acetylcholinesterase inhibitor, e.g. donepezil, rivastigmine or galantamine; and an antiglutamatergic agent, such as memantine.

In the case of Tourette's syndrome, the compound of the invention may be combined at least with one active agent selected from the group consisting of an alpha receptor agonist, such as clonidine;

an antipsychotic agent, such as fluphenazine, haloperidol, pimozide, aripirazole, of risperidone; and a dopamine depleting agent, such as tetrabenazine.

In the case of attention-deficit hyperactivity disorder, the compound of the invention may be combined at least with one active agent selected from the group consisting of a noradrenaline-dopamine reuptake inhibitor, such as modafinil or armodafinil;

a tri- or tetracyclic antidepressant, such as clomipramine;

a psychostimulant, such as methylphenidate a noradrenaline-serotonin reuptake inhibitor, such as venlafaxine or duloxetine;

a selective serotonin reuptake inhibitor, such as paroxetine; and a noradrenaline reuptake inhibitor, such as reboxetine or atomoxetine.

The compounds of the invention may be useful for the prevention of the above-mentioned conditions and disorders.

The compounds of the invention may be useful for the treatment of the above-mentioned conditions and disorders.

The compounds of the invention may be useful for the delay of progression of the above-mentioned conditions and disorders.

The usefulness of the compounds of the invention in the treatment of the above-mentioned disorders can be confirmed in a range of standard tests including those indicated below:

The in vivo activity of the compounds of the invention can be assessed by measuring the effects on brain histamine release (quantification of the histamine metabolite tele-methylhistamine) and/or by testing the effects on wakefulness in rats with EEG electrodes.

Compounds of the invention may be especially useful in the treatment of an indication selected from: narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

Thus, as a further embodiment, the invention provides the use of a compound of formula (I) or a pharmaceutically acceptable salt thereof as a medicament.

As a further embodiment, the invention provides the use of a compound of formula (I) or a pharmaceutically acceptable salt thereof in therapy.

In a further embodiment, the therapy is selected from a disease which is ameliorated by inhibition of H3 receptor action. In another embodiment, the disease is selected from the afore-mentioned list, e.g. is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

In another embodiment, the invention provides a method of treating a disease which is ameliorated by inhibition of H3 receptors comprising administration of a therapeutically acceptable amount of a compound of formula (I) or a pharmaceutically acceptable salt thereof. In a further embodiment, the disease is selected from the afore-mentioned list, e.g. is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

The term "a therapeutically effective amount" of a compound of the invention refers to an amount of the compound of the invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the invention that, when administered to a subject, is effective to (1) at least partially alleviating, inhibiting, preventing and/or ameliorating a condition, or a disorder or a disease (i) mediated by H3 receptors, or (ii) associated with H3 receptor activity, or (iii) characterized by abnormal activity of H3 receptors; or (2) reducing or inhibiting the activity of H3 receptors; or (3) reducing or inhibiting the expression of H3 receptors. In another non-limiting embodiment, the term "a therapeutically effective amount" refers to the amount of the compound of the invention that, when administered to a cell, or a tissue, or a non-cellular biological material, or a medium, is effective to at least partially reducing or inhibiting the activity of H3 receptors; or at least partially reducing or inhibiting the expression of H3 receptors.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

The pharmaceutical composition or combination of the invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between e.g. about 0.001-500 mg/kg, or between e.g. about 0.1-100 mg/kg.

The activity of a compound of the invention can be assessed by in vitro & in vivo methods described herein.

The compound of the invention may be administered either simultaneously with, or before or after, at least one other therapeutic agent. The compound of the invention may be administered separately, by the same or different route of administration, or together in the same pharmaceutical composition.

The following Examples illustrate the invention, but do not limit it.

ABBREVIATIONS

BINAP (+/−)-2,2'-Bis(diphenylphosphino)-1,1'-binaphthyl

Boc di(tert-butyl) carbonate

BTC triphosgene

DCM dichloromethane

DIPEA N-ethyl-N-isopropylpropan-2-amine (Diisopropylethylamine)

DMAP 4-Dimethylaminepyridine

EA ethyl acetate h hour(s)

HPLC high pressure liquid chromatography

LCMS liquid chromatography mass spectroscopy

MeOH methanol min minute(s)

NMR nuclear magnetic resonance spectrometry prep-HPLC preparative high pressure liquid chromatography $Pd_2(dba)_3$ tris(dibenzylideneacetone)dipalladium(0)

Rt retention time rt room temperature t-BuOK Potassium tert-butanolate

TEA triethylamine

TFA trifluoroacetic acid

THF tetrahydrofuran

LCMS Conditions (%=Percent by Volume):

Agilent 1200 HPLC/6110 SQ system; Mobile Phase: A: water (10 mM $NH_4HCO_3$) B: Acetonitrile; Gradient: 5% B for 0.2 min, increase to 95% B within 1.2 min; 95% B for 1.5 min, back to 5% B within 0.01 min; Flow Rate: 1.8 ml/min; Column: XBridge C18, 4.6*50 mm, 3.5 um; Oven Temperature: 50° C.

$^1$H NMR Instruments:

Bruker AVANCE III (500 MHz), Bruker AVANCE III (400 MHz)

EXAMPLES

Example 1.1

1-(6-oxo-1,6-dihydropyridazin-3-yl)piperidin-4-yl 4-cyclobutyl piperazine-1-carboxylate (Method A)

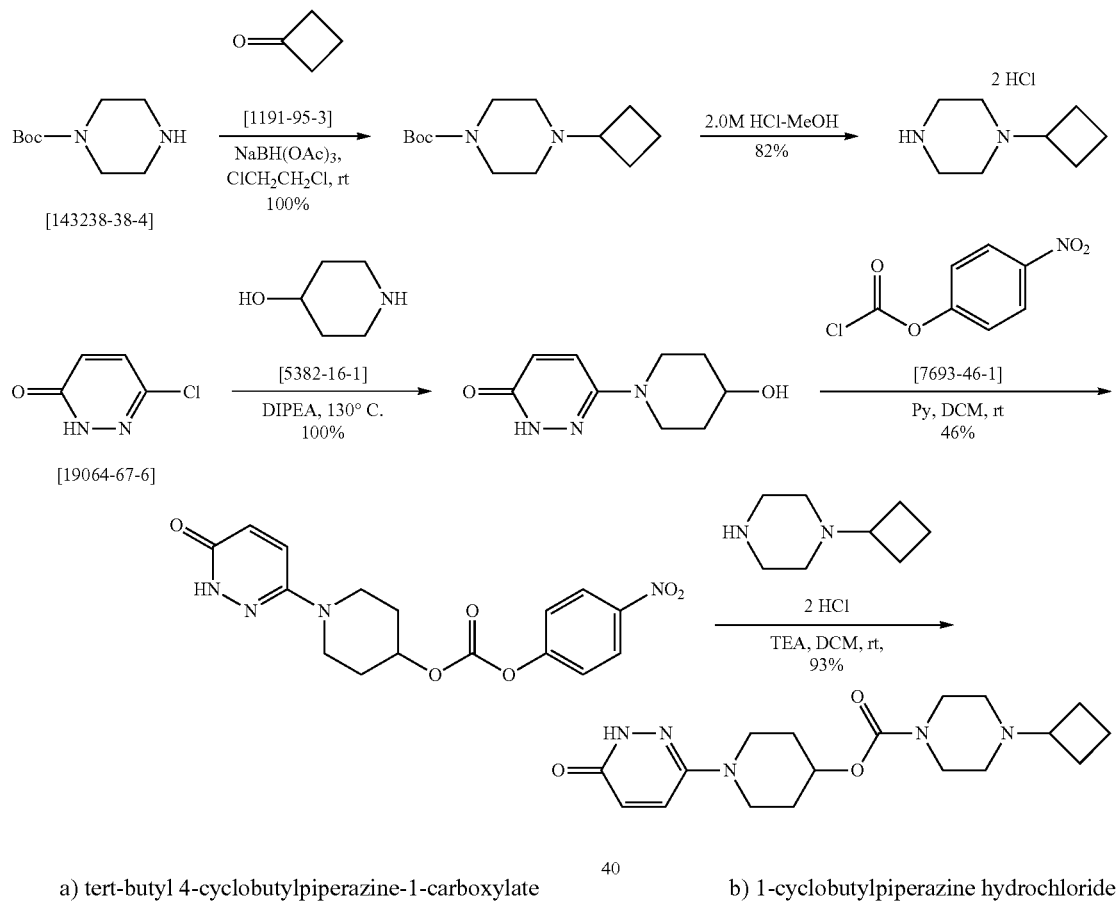

a) tert-butyl 4-cyclobutylpiperazine-1-carboxylate

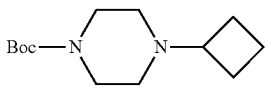 [SMILES: CC(C)(C)OC(=O)N1CCN(C2CCC2)CC1]

To a solution of compound tert-butyl piperazine-1-carboxylate (37.2 g, 200 mmol) in ClCH$_2$CH$_2$Cl (500 mL) was added cyclobutanone (21 g, 300 mmol) and NaBH(OAc)$_3$ (84.8 g, 400 mmol). The reaction mixture was stirred at rt for 16 h, quenched with saturated aq. Na$_2$CO$_3$ (500 mL) and extracted with DCM (3×500 mL). The combined organic layers were washed with brine (50 mL), dried, filtered and concentrated under reduced pressure to afford the desired compound tert-butyl 4-cyclobutylpiperazine-1-carboxylate (48 g, 100%) [LCMS: Rt=1.67 min, m/z 241.2 (M+H)$^+$].

b) 1-cyclobutylpiperazine hydrochloride

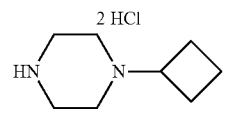

To the mixture of tert-butyl 4-cyclobutylpiperazine-1-carboxylate (48 g, 200 mmol) in MeOH (100 mL) was added 2.0 M HCl in MeOH (400 mL) carefully at 0° C. The mixture was stirred at rt for 5 h, concentrated under reduced pressure to afford the desired compound 1-cyclobutylpiperazine hydrochloride (35 g, 82%) [LCMS: Rt=0.94 min, m/z 141.3 (M+H)$^+$].

c) 6-(4-hydroxypiperidin-1-yl)pyridazin-3(2H)-one

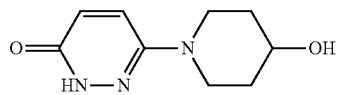

To a solution of 6-chloropyridazin-3(2H)-one (2.6 g, 20 mmol) in DIPEA (30 mL) was added piperidin-4-ol (2.4 g, 20 mmol) and the mixture was stirred at 120° C. for 8 h. The reaction mixture was concentrated under reduced pressure to afford the crude product, which was further purified by silica gel chromatography (DCM/MeOH=20/1) to afford the title compound (3.9 g, 100%) as a yellow solid. [LCMS: Rt=0.77 min, m/z 196.2 (M+H)+].

d) 4-nitrophenyl 1-(6-oxo-1,6-dihydropyridazin-3-yl) piperidin-4-yl carbonate

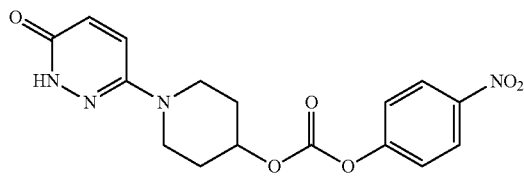 [SMILES: O=C(Oc1ccc([N+](=O)[O-])cc1)OC1CCN(c2ccc(=O)[nH]n2)CC1]

To a solution of 6-(4-hydroxypiperidin-1-yl)pyridazin-3 (2H)-one (3.9 g, 20 mmol) in pyridine (10 mL) was added DIPEA (3.87 g, 30.0 mmol) and 4-nitrophenyl carbonochloridate (6.03 g, 30 mmol) and the resulting mixture was stirred at 30° C. for 2 h. The mixture was concentrated under reduced pressure and the residue was purified by silica gel chromatography (DCM to DCM/MeOH=20/1) to afford the title compound (3.3 g, 46%) as a white solid. [LCMS: Rt=1.47 min, m/z 361.1 (M+H)+].

e) 1-(6-oxo-1,6-dihydropyridazin-3-yl)piperidin-4-yl 4-cyclobutylpiperazine-1-carboxylate

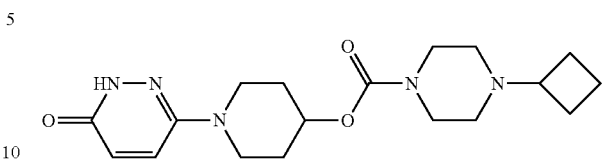

To a solution of 4-nitrophenyl 1-(6-oxo-1,6-dihydropyridazin-3-yl)piperidin-4-yl carbonate (440 mg, 1.22 mmol) in DCM (20 mL) was added TEA (616 mg, 6.1 mmol) and 1-cyclobutylpiperazine (388 mg, 1.83 mmol). The resulting mixture was stirred at 30° C. for 2 h before it was concentrated to dryness. The title compound was obtained as a white solid after silica gel chromatography (DCM/MeOH=50/1 to 5/1) (410 mg, 93%). [$^1$H NMR (400 MHz, CDCl$_3$) δ 11.20 (s, 1H), 7.20 (d, J=10 Hz, 1H), 6.87 (d, J=10 Hz, 1H), 4.87~4.92 (m, 1H), 3.45~3.50 (m, 6H), 3.16~3.23 (m, 2H), 2.68~2.76 (m, 1H), 2.29 (br, 4H), 1.72~2.07 (m, 10H); LCMS: Rt=1.36 min, m/z 362.3 (M+H)+].

Example 1.2

1-(1-methyl-6-oxo-1,6-dihydropyridazin-3-yl)piperidin-4-yl-4-isopropylpiperazine-1-carboxylate

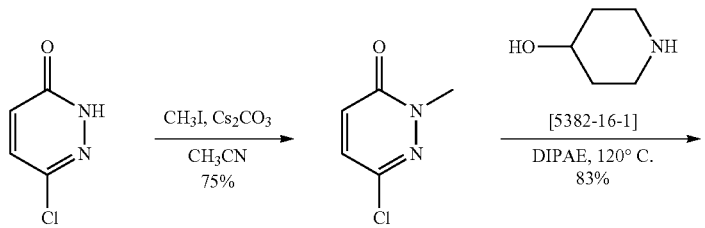

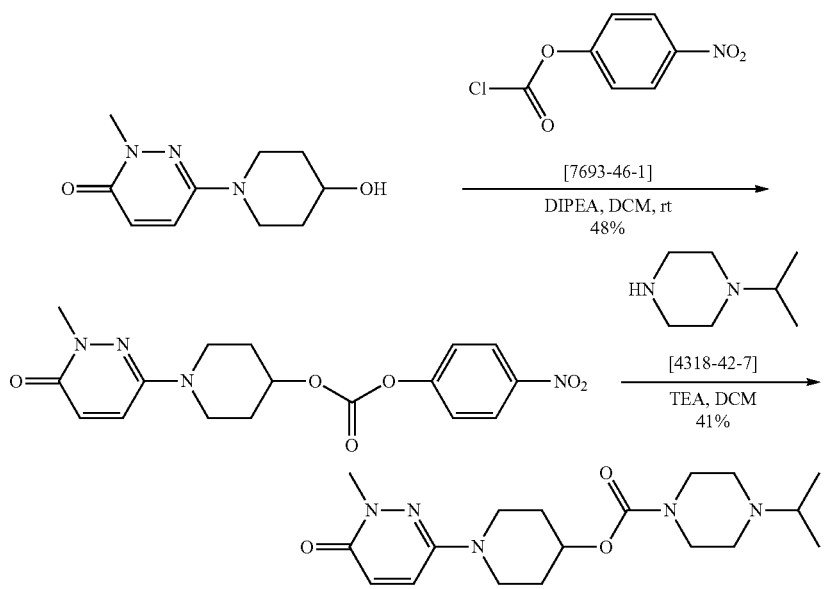

a) 6-chloro-2-methylpyridazin-3(2H)-one

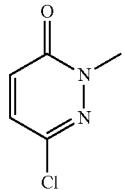

To a solution of 6-chloropyridazin-3(2H)-one (780 mg, 6 mmol) in CH$_3$CN (40 mL) was added Cs$_2$CO$_3$ (3.9 g, 12 mmol) and CH$_3$I (1 mL, 12 mmol) and the reaction mixture was stirred at 70° C. overnight. Solid was removed by filtration and the filtrate was concentrated under reduced pressure. The residue was purified by silica gel chromatography (hexane/EA=3/1) to afford the title compound as orange oil (6.5 g, 75%). [LCMS: Rt=1.43 min, m/z 145.1 (M+H)$^+$].

b) 6-(4-hydroxypiperidin-1-yl)-2-methylpyridazin-3(2H)-one

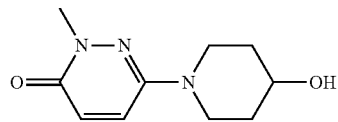

To a slurry of 6-chloro-2-methylpyridazin-3(2H)-one (1 g, 6.94 mmol) in DIPEA (20 mL) was added piperidin-4-ol (0.84 g, 8.33 mmol) and the reaction mixture was stirred at 120° C. overnight. The resulting mixture was diluted with water (30 mL) and extracted with DCM (3×30 mL) to remove impurities. The aqueous phase was concentrated to dryness to afford the title compound as a yellow solid (1.2 g, 83%). [LCMS: Rt=1.07 min, m/z 210.1 (M+H)$^+$].

c) 1-(1-methyl-6-oxo-1,6-dihydropyridazin-3-yl)piperidin-4-yl-4-nitrophenyl carbonate

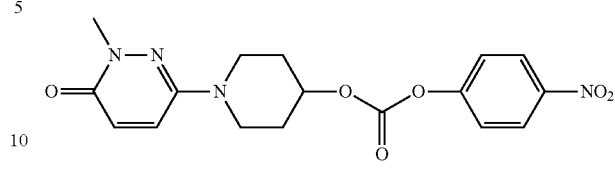

To a solution of 6-(4-hydroxypiperidin-1-yl)-2-methylpyridazin-3(2H)-one (1.46 g, 7 mmol) in DCM (20 mL) was added 4-nitrophenyl carbonochloridate (2.11 g, 10.5 mmol) and DIPEA (1.81 g, 14 mmol) and the mixture was stirred at rt overnight. The mixture was diluted with DCM (20 mL), washed with water (3×15 mL) and the organic layer was concentrated to afford the title compound as a yellow solid (1.2 g, 46%). [LCMS: Rt=1.54 min, m/z=375.1 (M+H)$^+$].

d) 1-(1-methyl-6-oxo-1,6-dihydropyridazin-3-yl)piperidin-4-yl-4-isopropylpiperazine-1-carboxylate

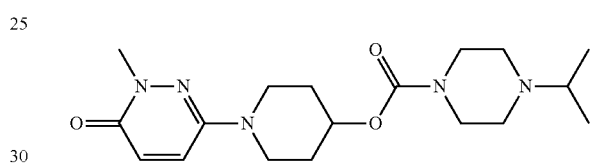

To a solution of 1-(1-methyl-6-oxo-1,6-dihydropyridazin-3-yl)piperidin-4-yl 4-nitrophenyl carbonate (1.2 g, 3.2 mmol) in DCM (20 mL) was added 1-isopropylpiperazine (0.6 g, 4.8 mmol) and TEA (5 mL) and the reaction mixture was stirred at rt overnight. The mixture was then washed with saturated Na$_2$CO$_3$ (3×30 mL), dried and concentrated to give crude product, which was purified by silica gel chromatography (PE/EA=1/1) to afford the title compound as a white solid (0.48 g, 41%). [$^1$H NMR (CDCl$_3$, 400 MHz): δ7.13~7.10 (d, J=10, 1H), 6.86~6.84 (d, J=10, 1H), 4.92~4.88 (m, 1H), 3.66 (s, 3H), 3.51~3.46 (br, 6H); 3.22~3.16 (m, 2H); 2.74~2.70 (m, 1H), 2.49 (br, 4H), 1.99 (m, 2H), 1.75 (m, 2H), 1.04 (d, 6H); LCMS Rt=1.40 min, m/z 364.2 (M+H)$^+$].

Example 1.5

1-(1-methyl-6-oxo-1,6-dihydropyridazin-3-yl)piperidin-4-yl 4-cyclobutylpiperazine-1-carboxylate

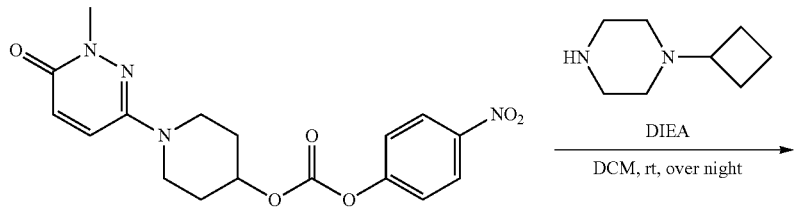

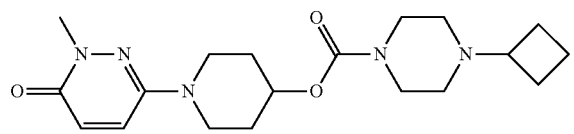 [SMILES: Cn1nc(N2CCC(OC(=O)N3CCN(C4CCC4)CC3)CC2)ccc1=O]

a) 1-(1-methyl-6-oxo-1,6-dihydropyridazin-3-yl)-piperidin-4-yl-4-cyclobutyl-piperazine-1-carboxylate

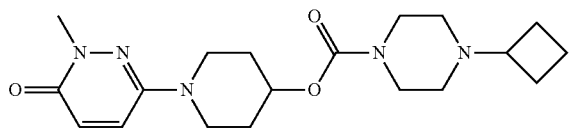

To a solution of 1-(1-methyl-6-oxo-1,6-dihydropyridazin-3-yl) piperidin-4-yl 4-nitrophenyl carbonate (101 mg, 0.27 mmol) in 8 mL of DCM, was added DIEA (105 mg, 0.81 mmol) and 1-cyclobutylpiperazine (56 mg, 0.40 mmol). The mixture was stirred at rt over night before it was diluted with 30 mL of water, extracted with DCM (3*25 mL). The combined organic phase was dried over anhydrous $Na_2SO_4$, filtered and concentrated under reduced pressure. The residue was purified via Flash (Biotage, reversed phase column C-18, MeOH/$H_2O$=5%-95%, 0.5% $NH_4OH$) to afford 20 mg of the desired compound as a white solid. CH NMR (CDCl$_3$, 400 MHz): δ7.12 (d, J=10, 1H), 6.85 (d, J=10, 1H), 4.94-4.88 (m, 1H), 3.67 (s, 3H), 3.52-3.46 (m, 6H), 3.23-3.17 (m, 2H), 2.75-2.69 (m, 1H), 2.30 (b, 4H), 2.08-1.97 (m, 4H), 1.93-1.86 (m, 2H), 1.82-1.68 (m, 4H); LCMS Rt=1.44 min, m/z 376.3 (M+H)$^+$].

Example 2

Synthesis of 1-(1-methyl-6-oxo-1,6-dihydropyrimidin-4-yl)piperidin-4-yl-4-isopropylpiperazine-1-carboxylate (Method B)

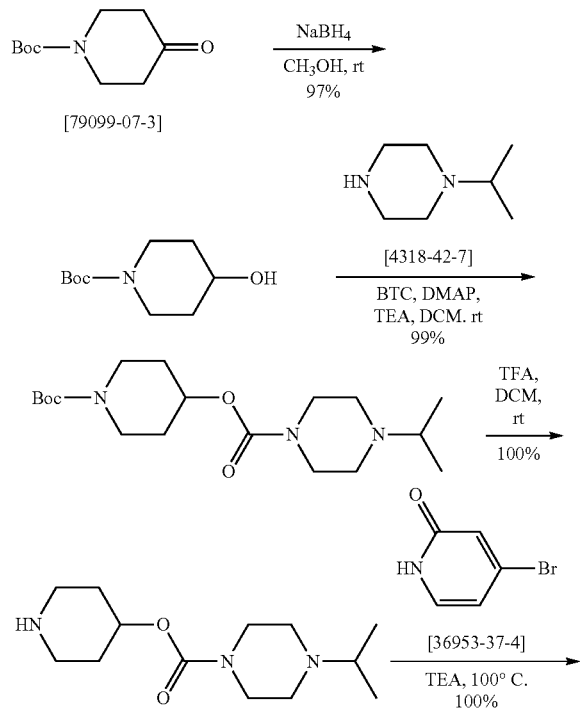

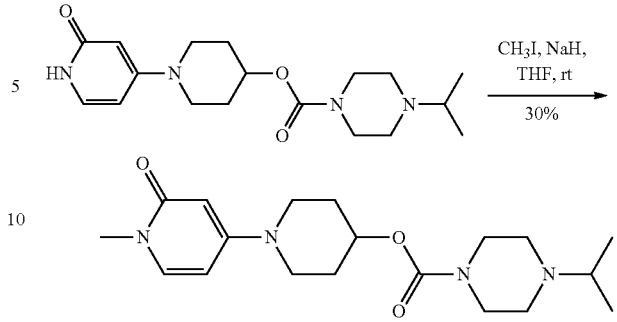

a) tert-butyl 4-hydroxypiperidine-1-carboxylate

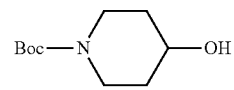

To a solution of tert-butyl 4-oxopiperidine-1-carboxylate (10 g, 50 mmol) in $CH_3OH$ (100 mL) was added $NaBH_4$ (5.7 g, 150 mmol) portionwise carefully and the mixture was stirred at rt for 3 h. The reaction was quenched by carefully pouring into ice-water (100 mL) and organic solvent was removed under reduced pressure. The aqueous phase was neutralized to pH=7 with 1N HCl and extracted with DCM/MeOH (5×60 mL, v/v=10/1). The combined organic layers were washed with brine (30 mL), dried over anhydrous $Na_2SO_4$, filtered and concentrated under reduced pressure to afford the crude product (9.8 g, 97%) as a white solid. [LCMS: Rt=1.36 min, m/z 146.1 (M−Bu+H)$^+$].

a) 1-(tert-butoxycarbonyl)piperidin-4-yl 4-isopropylpiperazine-1-carboxylate

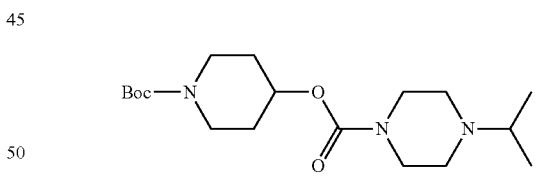

To a solution of tert-butyl 4-hydroxypiperidine-1-carboxylate (4.4 g, 21.9 mmol) in DCM (100 mL) was carefully added DMAP (5.3 g, 43.8 mmol) and triphosgene (3.2 g, 10.95 mmol) portionwise. After stirring at rt for 2 h, 1-isopropylpiperazine (3.3 g, 26 mmol) was added and the reaction mixture was stirred at rt for 5 h. The reaction was quenched with saturated $NH_4Cl$ (100 mL) solution and the mixture was extracted with DCM (3×100 mL). The combined organic layers were washed with saturated $NH_4Cl$ (2×100 mL) and brine (50 mL) sequentially, dried over anhydrous $Na_2SO_4$, filtered and concentrated under reduced pressure to afford the title compound as a white solid (7.7 g, 99%). [LCMS: Rt=1.67 min, m/z 356.3 (M+H)$^+$].

b) piperidin-4-yl 4-isopropylpiperazine-1-carboxylate

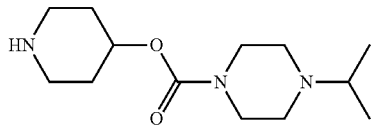 [SMILES: CC(C)N1CCN(C(=O)OC2CCNCC2)CC1]

To a solution of 1-(tert-butoxycarbonyl)piperidin-4-yl 4-isopropyl piperazine-1-carboxylate (7.7 g, 21.7 mmol) in DCM (30 mL) was added TFA (10 mL) and the reaction mixture was stirred at rt for 5 h. The solvent was removed under reduced pressure and the residue was re-dissolved in DCM/MeOH (100 mL, v/v=10/1). Then powder $Na_2CO_3$ was added and the mixture was stirred at rt for 2 h. Excess $Na_2CO_3$ was removed by filtration and the cake was washed with DCM (2×100 mL). The combined filtrates were concentrated under reduced pressure to afford the desired compound as yellow oil (5.5 g, 100%). [LCMS: Rt=1.12 min, m/z 256.2 $(M+H)^+$].

c) 1-(2-oxo-1,2-dihydropyridin-4-yl)piperidin-4-yl-4-isopropylpiperazine-1-carboxylate

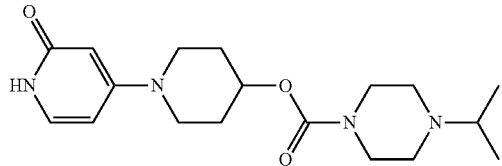

To a solution of 4-bromopyridin-2(1H)-one (173 mg, 1.0 mmol) in TEA (10 mL) was added piperidin-4-yl-4-isopropylpiperazine-1-carboxylate (255 mg, 1.0 mmol) and the mixture was stirred at 100° C. for 16 h. After cooling to rt, the mixture was concentrated under vacuum. The residue was dissolved in DCM (50 mL) and the mixture was washed with saturated $NaHCO_3$ solution (2×30 mL). The organic layer was dried and concentrated to afford the crude product (348 mg, 100%), which was used directly for next step without further purification. [LCMS: Rt=1.27 min, m/z 349.2 $(M+H)^+$].

d) 1-(1-methyl-6-oxo-1,6-dihydropyrimidin-4-yl) piperidin-4-yl-4-isopropylpiperazine-1-carboxylate

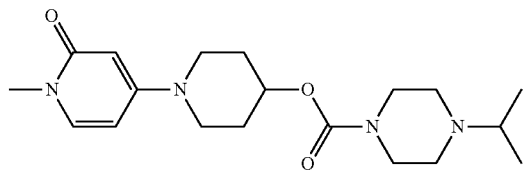

To a solution of 1-(2-oxo-1,2-dihydropyridin-4-yl)piperidin-4-yl 4-isopropylpiperazine-1-carboxylate (348 mg, 1.0 mmol) in THF (10 mL) was added NaH (60% in mineral oil) (200 mg, 5.0 mmol) portionwise. After stirring at rt for 1 h, $CH_3I$ (213 mg, 1.5 mmol) was added and the reaction mixture was stirred at rt for 5 h. The reaction was quenched with water (30 mL), extracted with DCM (3×30 mL), dried and concentrated to give crude product, which was further purified by prep-HPLC to afford the title compound as a white solid (110 mg, 30%). CH NMR (500 MHz, $CDCl_3$) δ7.07 (d, J=8.0 Hz, 1H), 5.90 (dd, J=8.0, 2.5 Hz, 1H), 5.77 (d, J=2.5 Hz, 1H), 4.89~4.94 (m, 1H), 3.47~3.52 (m, 6H), 3.44 (s, 3H), 3.20~3.25 (m, 2H), 2.68~2.73 (m, 1H), 2.47 (br, 4H), 1.92~1.98 (m, 2H), 1.69~1.76 (m, 2H), 1.04 (d, J=6.5 Hz, 6H); LCMS: Rt=1.31 min, m/z 363.3 $(M+H)^+$].

Example 3

1-(6-oxo-1,6-dihydropyridin-3-yl)piperidin-4-yl-4-isopropylpiperazine-1-carboxylate (Method C)

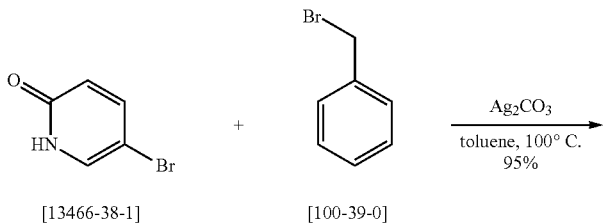

[13466-38-1]   [100-39-0]

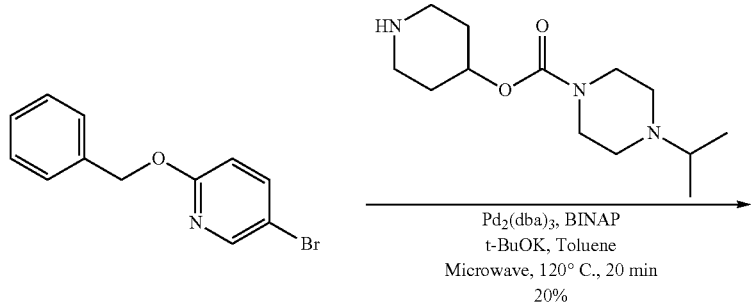

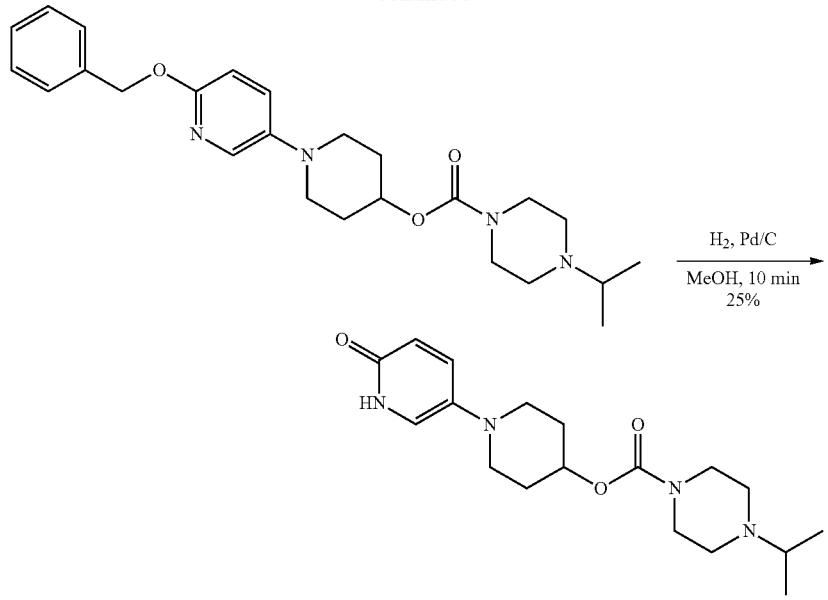

a) 2-(benzyloxy)-5-bromopyridine

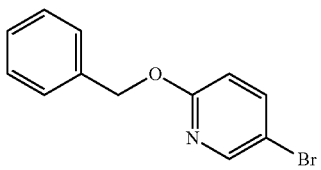 [SMILES: Brc1ccc(OCc2ccccc2)nc1]

To a solution of 5-bromopyridin-2(1H)-one (1.28 g, 7.36 mmol) and Ag$_2$CO$_3$ (3 g, 11.04 mmol) in toluene (50 mL) was added (bromomethyl)benzene (1.25 g, 7.36 mmol) dropwise and the reaction mixture was stirred at 100° C. over night. The reaction mixture was filtered through a short pad of silica gel and washed with DCM. The filtrate was concentrated to yield the title compound as light yellow oil (1.8 g, 95%).

b) 1-(6-(benzyloxy)pyridin-3-yl)piperidin-4-yl 4-isopropylpiperazine-1-carboxylate

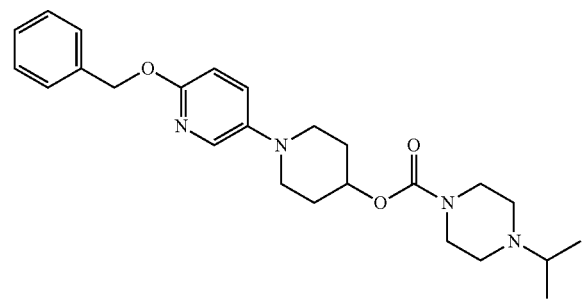 [SMILES: CC(C)N1CCN(C(=O)OC2CCN(c3ccc(OCc4ccccc4)nc3)CC2)CC1]

To a solution of 2-(benzyloxy)-5-bromopyridine (1.5 g, 5.6 mmol), piperidin-4-yl 4-isopropylpiperazine-1-carboxylate (2.15 g, 8.4 mmol) in toluene (30 mL) was added Pd$_2$(dba)$_3$ (1.57 g, 2.2 mmol), BINAP (2.79 g, 4.4 mmol) and t-BuOK (3.78 g, 33.8 mmol). The reaction was stirred under the microwave irradiation at 120° C. for 20 min. The mixture was diluted with EA (100 mL) and washed with water (3×50 mL). The organic phase was separated, dried and concentrated to dryness. The residue was taken into dilute HCl (pH=1, 100 mL) and the mixture was extracted with DCM (3×100 mL) to remove impurities. The aqueous phase was made basic (pH=9-10) with solid Na$_2$CO$_3$ and extracted with DCM (3×100 mL). The combined organic layers were dried, concentrated and purified by silica gel chromatography (EA/MeOH=50/1) to give the title compound as a white solid (500 mg, 20%). [LCMS: Rt=2.09 mim, m/z 439.3 (M+H)$^+$].

c) 1-(6-oxo-1,6-dihydropyridin-3-yl)piperidin-4-yl-4-isopropylpiperazine-1-carboxylate

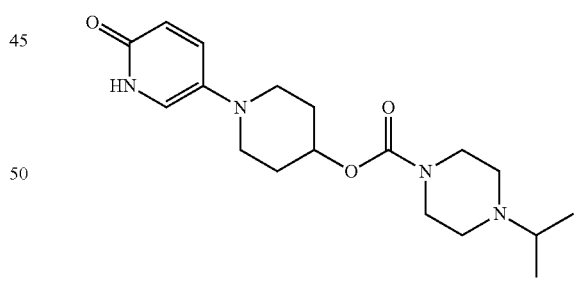

To a suspension of 1-(6-(benzyloxy)pyridin-3-yl)-piperidin-4-yl-4-isopropylpiperazine-1-carboxylate (200 mg, 0.46 mmol) in MeOH (10 mL) was added 10% Pd/C (200 mg) and the mixture was hydrogenated (hydrogen balloon) at rt for 10 min. The catalyst was removed by filtering through Celite® and the filtrate was concentrated under vacuum. The desired product was obtained as a white solid after pre-HPLC purification (40 mg, 25%). CH NMR (400 MHz, MeOD-d$_4$) δ 7.50 (dd, J=10 Hz, J$_2$=3.2 Hz, 1H), 6.81 (d, J=3.2 Hz, 1H), 6.41 (d, J=10 Hz, 1H), 4.68 (m, 1H), 3.45 (br, 4H), 3.00 (m, 2H), 2.75 (m, 3H), 2.59 (m, 4H), 1.90 (m, 2H), 1.70 (m, 2H), 1.02 (d, J=6.4 Hz, 6H); LCMS: Rt=1.37 min, m/z 349.2 (M+H)$^+$].

Table 1 shows compounds of formula (I). Examples 1.1 to 1.6 were synthesized according to Method A; Examples 2.1 to 2.3 were synthesized according to Method B; Example 3.1 was synthesized according to Method C.

TABLE 1

| Ex. | Structure | Name | LCMS Rt [min], method | [M + H]+ |
|---|---|---|---|---|
| 1.1 | 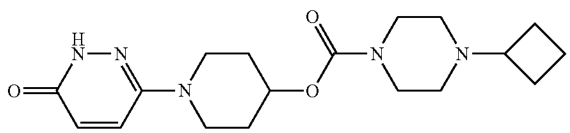 [SMILES: O=C(OC1CCN(c2ccc(=O)[nH]n2)CC1)N1CCN(C2CCC2)CC1] | 1-(6-oxo-1,6-dihydropyridazin-3-yl)piperidin-4-yl 4-cyclobutylpiperazine-1-carboxylate | 1.65(A) | 362.2 |
| 1.2 | 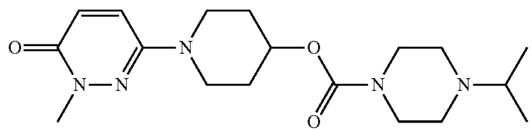 [SMILES: CC(C)N1CCN(C(=O)OC2CCN(c3ccc(=O)n(C)n3)CC2)CC1] | 1-(1-methyl-6-oxo-1,6-dihydropyridazin-3-yl)piperidin-4-yl 4-isopropylpiperazine-1-carboxylate | 1.4(A) | 364.2 |
| 1.3 | 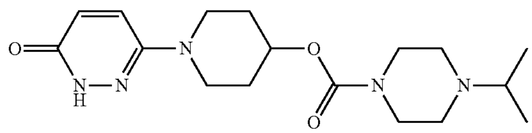 [SMILES: CC(C)N1CCN(C(=O)OC2CCN(c3ccc(=O)[nH]n3)CC2)CC1] | 1-(6-oxo-1,6-dihydropyridazin-3-yl)piperidin-4-yl 4-isopropylpiperazine-1-carboxylate | 1.33(A) | 350.2 |
| 1.4 | 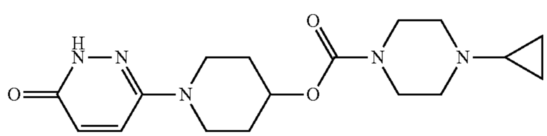 [SMILES: O=C(OC1CCN(c2ccc(=O)[nH]n2)CC1)N1CCN(C2CC2)CC1] | 1-(6-oxo-1,6-dihydropyridazin-3-yl)piperidin-4-yl 4-cyclopropylpiperazine-1-carboxylate | 1.05(A) | 348.2 |
| 1.5 | 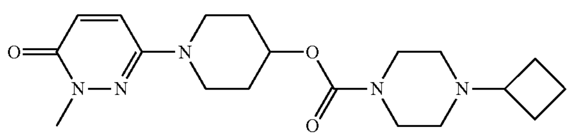 [SMILES: Cn1nc(N2CCC(OC(=O)N3CCN(C4CCC4)CC3)CC2)ccc1=O] | 1-(1-methyl-6-oxo-1,6-dihydropyridazin-3-yl)piperidin-4-yl 4-cyclobutylpiperazine-1-carboxylate | 1.44(A) | 376.3 |
| 1.6 | 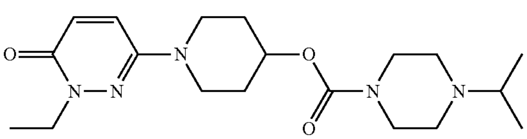 | 1-(1-ethyl-6-oxo-1,6-dihydropyridazin-3-yl)piperidin-4-yl 4-isopropylpiperazine-1-carboxylate | 0.87(A) | 378.2 |
| 2.1 | 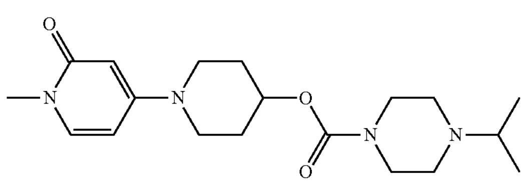 [SMILES: CC(C)N1CCN(C(=O)OC2CCN(c3ccn(C)c(=O)c3)CC2)CC1] | 1-(1-methyl-2-oxo-1,2-dihydropyridin-4-yl)piperidin-4-yl 4-isopropylpiperazine-1-carboxylate | 1.31(B) | 363.3 |
| 2.2 | 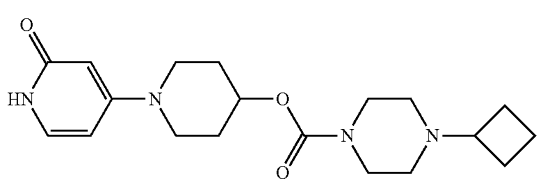 [SMILES: O=C(OC1CCN(c2cc[nH]c(=O)c2)CC1)N1CCN(C2CCC2)CC1] | 1-(2-oxo-1,2-dihydropyridin-4-yl)piperidin-4-yl 4-cyclobutylpiperazine-1-carboxylate | 1.31(B) | 361.2 |
| 2.3 | 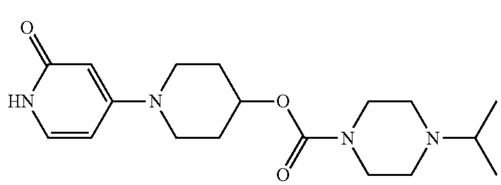 [SMILES: CC(C)N1CCN(C(=O)OC2CCN(c3cc[nH]c(=O)c3)CC2)CC1] | 1-(2-oxo-1,2-dihydropyridin-4-yl)piperidin-4-yl 4-isopropylpiperazine-1-carboxylate | 1.26(B) | 349.2 |

TABLE 1-continued

| Ex. | Structure | Name | LCMS Rt [min], method | [M + H]+ |
|---|---|---|---|---|
| 3.1 | 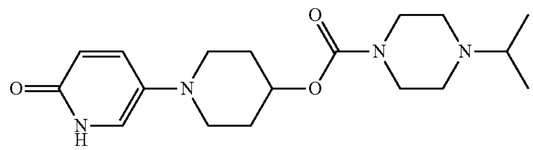 [SMILES: CC(C)N1CCN(C(=O)OC2CCN(c3ccc(=O)[nH]c3)CC2)CC1] | 1-(6-oxo-1,6-dihydropyridin-3-yl)piperidin-4-yl 4-isopropylpiperazine-1-carboxylate | 1.37(C) | 349.2 |

Biological Testing
1.1 In-vitro Testing
A) Potency Assessment

The potency of compounds of the invention as H3 receptor antagonists can be assessed by measuring the blockade of (R)-alpha-methylhistamine-mediated cAMP production utilizing a LANCE Ultra cAMP kit (PE #TRF0263) in CHO cells expressing human H3 receptors (GenBank: BC096840; Strausberg R L et al, Proc. Natl. Acad. Sci. U.S.A. 99(26), 16899-16903; 2002).

Protocol:
1. Preparation of the stimulation buffer (30 ml): 29.4 ml HBSS (GIBCO #14025), 150 µl 1 M HEPES (GIBCO #15630), 30 µl 500 mM IBMX (CALBIOCHEM #410957) and 400 µl 7.5% BSA (GIBCO #10438-026).
2. Preparation of assay plate: Different concentrations of the compounds of the invention (0.01-1000 nM), H3 positive controls and cAMP calibration standards; 3 mM Forskolin (CALBIOCHEM #344270); 5 µM (R)-alpha-methylhistamine (H3 receptor agonist); 1% DMSO (SIGMA #D2650); total volume: 95 nl.
3. Preparation of the cell solution: Collect cells with stimulation buffer, final density: 100,000 cells/ml.
4. Reaction: (a) transfer 10 µl of cell solution to assay plate, (b) centrifuge at 600 rpm for 3 min and incubate 50 min at room temperature, (c) add 5 µL 4×Eu-cAMP tracer solution (60 µl Eu-cAMP tracer stock solution+2.94 ml cAMP detection buffer) and 5 µL 4×ULight™-anti-cAMP solution (20 µl Eu-cAMP tracer stock solution+2.98 ml cAMP detection buffer) to assay plate.
5. Reading plate on EnVision: flash energy: 100%; excitation filter: 111 UV2 320; emission filter: 203 (Eu 615) and 205 (APC 665); number of laser flashes: 20; window: 100 µs; laser mirror module: 445 or 446; laser cycle: 16,600 µs.
6. Data analysis by Graph Pad Prism: log (compound concentration) vs. response; variable slope.

B) Affinity Assessment

The affinity of compounds of the invention to the H3 receptor can be assessed by measuring displacement of binding of the radioligand [3H]-N-α-Methylhistamine (PerkinElmer, #NET1027250UC) to membranes containing human H3 receptors (PerkinElmer, #ES-392-M400UA; GenBank: NM_007232.2; Hill S J et al, International Union of Pharmacology XIII. Classification of histamine receptors, Pharmacol Rev, 49(3), 253-278, 1997).

Protocol:
1. Preparation of binding assay buffer (500 ml): 25 ml 1 M Tris-HCl pH 7.5 (Invitrogen, #15567-027), 2.5 ml 1 M MgCl2 (Sigma, #M1028-100ML), 472.5 ml ddH2O.
2. Compound serial dilution: Dilution was performed by BioTek Precision on compound dilution plate. Compound concentrations start at 5 or 10 µM, 10 point dose titrations with 3- or 5-fold serial dilutions.
3. Preparation of 2× membrane solution (25 ml): 1.25 ml human Histamine H3 receptor stock, 23.75 ml assay buffer.
4. Preparation of 2× solution of [3H]—N-α-methylhistamine (25 ml): 4.27 µl [3H]—N-α-methylhistamine stock, 25 ml assay buffer.
5. Assemble binding reaction: (a) transfer 1 µl of compound solution, 1 µl 100% DMSO and 1 µl 1 M (R)(-)-α-Methylhistamine (Sigma, #H128) to the reaction plate at room temperature, (b) transfer 50 µl of 2× protein solution to reaction plate, (c) transfer 49 µl of 2× radioligand solution to reaction plate (Corning® 96 well EIA/RIA plate; Sigma, #CLS3797).
6. Cover the reaction plate with a TopSeal™-A film (Perkin Elmer, #6005185) and incubate at 28° C. for 120 min. Equilibrate Zeba Spin Desalting Plates (Thermo Scientific, #89808) to room temperature for 120 min.
7. Remove the sealing material from the bottom of the filtration plate. Place the plate on a wash plate. Centrifuge at 1000 g for 2 min to remove the storage buffer at room temperature.
8. Transfer 70 µl binding reaction from reaction plate into filtration plates. Place the filtration plates on top of collection plate. Centrifuge the plate assembly at 1000 g for 2 min to collect the protein with bound radioligand. Add 200 µl of Microscint-40 (PerkinElmer, #6013641-1L) to each well of the collection plate. Cover the plates with TopSeal™-A film.
9. Read the plates on Wallac Microbeta Trilux 2450, Instrument settings: counting mode: CPM, counting time: 2 min.
10. Data analysis: GraphPad Prism: log(compound concentration) vs. response; variable slope. The Ki is calculated based on Chang and Prusoff: Ki=IC50/{1+([radioligand]/Kd)}

Table 2 represents Ki values from above described potency/affinity assessments of compounds of the invention against human H3 receptors.

TABLE 2

| Example | Potency Ki (nM) | Affinity Ki (nM) |
|---|---|---|
| 1.1 | 1.3 | 26 |
| 1.2 | 2.4 | 31 |
| 1.3 | 1.2 | 10 |
| 1.4 | 2.3 | 25 |
| 1.5 | 1.1 | 25 |
| 1.6 | 2.9 | 44 |
| 2.1 | 3.1 | 20 |
| 2.2 | 0.5 | 25 |
| 2.3 | 0.9 | 12 |
| 3.1 | 1.6 | 1.2 |

1.2 In-Vivo Testing
A) Effects on Brain Tele-Methylhistamine Levels

Compounds of the invention were dissolved in 20% 2-hydroxyl-beta-cyclodextran (HBC) and then sonicated briefly until there is little or no suspension in the solution. Animals (male Sprague-Dawley rats at the age of 8 weeks) were orally dosed with test compounds 1 hour or other longer time points before they were sacrificed using $CO_2$.

Blood Sample Collection:

A cardiac puncture was performed to collect blood sample from the cardiac cavity. The collected blood was immediately mixed with EDTA-K2 20 μl/ml to avoid blood clotting. The blood samples in tubes were then centrifuged (15 mim, 6000 rpm) and the plasma transferred to new tubes and then temporarily kept in dry ice until they were stored in a –70° C. freezer.

CSF collection: CSF samples were taken from the foramen magnum of the animal (using a #0.5 intravenous needle), and the CSF sample were kept in dry ice.

Brain Tissue Collection:

The rat brain were taken out of the skull and rinsed with ice-cold saline first. The frontal cortex was separated from the rest of the brain on top of a petri dish with ice underneath. The wet weight of the frontal cortex was weighed and recorded immediately. The frontal cortex sample was then kept in dry ice until they are transferred to a –70° C. freezer.

Bioanalytical Methods for Tele-Methyl Histamine and Compounds:

Instrument: Agilent 6410, triple quadrupole mass spectrometer

Matrix: rat plasma, frontal cortex homogenate and cerebrospinal fluid (CSF)

Analyte: H3 compounds.

Internal standard: Dexamethasone

HPLC Conditions Mobile Phase A: H2O— 0.1% NH3.H2O:

Mobile phase B: MeOH-0.1% NH3.H2O

Column: Ultimate XB-C18 (2.1×50 mm, 5 μm)

Flow rate: 0.45 mL/min, temperature: 40° C.

MS Conditions:

ESI: positive ion

MRM detection

Dexamethasone: [M+H]+m/z 393.3→373.2; CE:4; Fragmentor:110

Sample Preparation:

Frontal Cortex: the brain sample was homogenized for 2 min with 3 volumes (v/w) of homogenizing solution (EtOH:PBS=85:15), and then centrifuged at 12,000 rpm for 5 min. The 30 μL supernatant of brain homogenate sample was added with 30 μL of the internal standard (Dexamethasone, 300 ng/mL) and then followed by 150 μL ACN for protein precipitation. The mixture was vortexed for 2 min and centrifuged at 12000 rpm for 5 min. The 5 μL supernatant was injected onto LC-MS/MS for analysis.

Plasma and CSF: an aliquot of 30 μL sample was added with 30 μL of the internal standard (300 ng/mL Dexamethasone) and then followed by 150 μL ACN for protein precipitation. The mixture was vortexed for 2 min and centrifuged at 12000 rpm for 5 min. The 5 μL supernatant was injected onto LC-MS/MS for analysis.

Table 3 represents data from measurements of the telemethylhistamine level in brain.

TABLE 3

| Example | % change in telemethylhistamine brain levels for 10 mg/kg @ 1 h |
|---|---|
| 1.1 | 72 |
| 1.2 | 138 |
| 1.3 | 115 |

B) Effects on Wakefulness

Animals: Male Sprague-Dawly rats (280-320 g) were were housed individually under an ambient temperature of 22±0.5° C. with a relative humidity of 60±2% and an automatically controlled 12-h light/12-h dark cycle (light on at 07:00, illumination intensity=100 lux). The animals had free access to food and water.

EEG recording set up, Polygraphic Recordings and Vigilance State Analysis: Under pentobarbital anesthesia (50 mg/kg, i.p.), rats were chronically implanted with EEG and electromyogram (EMG) electrodes for polysomnographic recordings (Huang et al, J Neurosci, 23, 5975-5983, 2003). Two stainless steel screws (1 mm in diameter) EEG electrodes (the first screw: anteroposterior (AP), +2 mm; left-right (LR), –2 mm; and the second: AP, –2 mm; LR, –2 mm, AP from bregma, LR from lambda) and a reference electrode (opposite to EEG screw side, AP, +3 mm; LR, 3 mm) were surgically implanted and 3 stainless steel screws for anchorage to the skull. Two insulated stainless steel, Teflon-coated wires were bilaterally placed into both trapezius muscles and served as EMG electrodes for rats. All electrodes were attached to a micro connector and fixed to the skull with dental cement.

The EEG and EMG recordings were carried out by means of a slip ring designed so that behavioral movement of the rat would not be restricted. After an 8-day recovery period, the rats were housed individually in transparent barrels and habituated to the recording cable for 3-4 days before polygraphic recording.

For the study of spontaneous sleep-wakefulness cycles, each animal was recorded for 24 h beginning at 19:00 P.M., the offset of the light period. The animals then entered the pharmacological phase of the study, in which sleep-wakefulness parameters were recorded for 72 h. The data collected during the first 24 h also served as baseline comparison data for the second experimental day.

Cortical EEG and EMG signals were amplified, filtered (EEG, 0.5-30 Hz; EMG, 20-200 Hz), digitized at a sampling rate of 128 Hz, and recorded by using SLEEPSIGN (Kissei Comtec, Nagano, Japan). When complete, polygraphic recordings were automatically scored offline by 4-sec epochs as wake, REM, and NREM sleep by SleepSign according to standard criteria (Huang et al, Nat Neurosci, 8, 858-859, 2005). As a final step, defined sleep-wake stages were examined visually and corrected, if necessary. EEG power density curve was plotted for each stage during 4 h after drug administration. The power of each 0.25 Hz bin was averaged across the sleep or wake stage and normalized as a group by calculating the percentage of each bin from the total power (0.25-25 Hz).

Pharmacological Treatments: Tested compounds, caffeine (positive reference compound) or compounds of the invention were prepared in 20% 2-hydroxyl-beta-cyclodextran (HBC). On the vehicle-treated day, all animals were administered with vehicle at 9:00 A.M. On the drug-treated day, the test compound, caffeine, or vehicle was given at 9:00 A.M. Thereafter, continuous recording was kept to the 3rd day. The volume was injected oral, or intraperitoneally at 2 ml/kg. Separate groups of rats were used for each dose (n=8 rats per group).

Time-course changes in the amounts of sleep-wake, sleep/wake stage transition number, as well as number and duration of sleep/wake bouts in light/dark phases, were analyzed by the paired t test, with each animal serving as its own control.

Table 4 represents data from measurements of percent increase in wakefulness in rats. Date is given for first 4 hours after oral compound administration.

TABLE 4

| Example | % increase in wakefulness at 10 mg |
|---------|-----------------------------------|
| 1.1     | 42.1                              |
| 1.2     | 48.8                              |
| 1.3     | 19.1                              |

*p < 0.5, **p < 0.01 (comparison with vehicle group)

In one embodiment, the invention provides a method of inhibiting H3 receptors in a subject, wherein the method comprises administering to the subject a therapeutically effective amount of a compound of formula I or a pharmaceutically acceptable salt thereof.

In a further embodiment, the invention provides a method of treating a disorder or a disease in a subject mediated by H3 receptors, wherein the method comprises administering to the subject a therapeutically effective amount of a compound of formula I or a pharmaceutically acceptable salt thereof. Preferably said disorder or said disease is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

In yet a further embodiment, the invention provides the use of a compound of formula I or a pharmaceutically acceptable salt thereof, for the treatment of a disorder or disease in a subject mediated by H3 receptors.

In yet a further embodiment, the invention provides the use of a compound of formula I or a pharmaceutically acceptable salt thereof, for the treatment of a disorder or disease in a subject characterized by an abnormal activity of H3 receptors. Preferably said disorder or said disease is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

In yet a further embodiment, the invention provides the use of a compound of formula I or a pharmaceutically acceptable salt thereof, for the treatment of a disorder or disease in a subject associated with irregularities of H3 receptor-modulated signal transmission. Preferably said disorder or said disease is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

II. Solid Forms of Carbamate Derivatives

The present invention also relates to solid forms of 1-(1-methyl-6-oxo-1,6-dihydropyridazin-3-yl)piperidin-4-yl 4-cyclobutylpiperazine-1-carboxylate and to pharmaceutical compositions comprising them, and to their use as medicaments.

The compound 1-(1-methyl-6-oxo-1,6-dihydropyridazin-3-yl)piperidin-4-yl 4-cyclobutylpiperazine-1-carboxylate of the formula IA

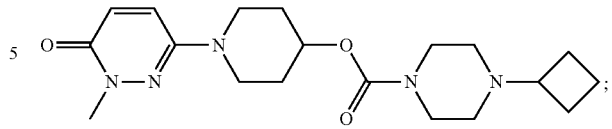

(IA)

is described hereinbefore.

Selection criteria for solid forms depend on the planned indications and route(s) of administration. For a CNS-indication, such as narcolepsy, with an envisaged oral route of administration it is important to e.g. achieve a good absorption/oral bioavailability. Especially suitable solid forms are crystalline forms having a low hygroscopy, a high aqueous solubility, a high melting point and do not exist in multiple forms (e.g. polymorphs, solvates and/or hydrates). Further relevant parameters are safety aspects (e.g. low toxicity), stability in bulk, compatibility with excipients, pH of aqueous solution, good morphology and easy handling.

The invention provides the free form of 1-(1-methyl-6-oxo-1,6-dihydropyridazin-3-yl)piperidin-4-yl 4-cyclobutylpiperazine-1-carboxylate in solid form. The invention further provides a salt of 1-(1-methyl-6-oxo-1,6-dihydropyridazin-3-yl)piperidin-4-yl 4-cyclobutylpiperazine-1-carboxylate in solid form, wherein said salt is the citrate, hydrochloride, fumarate, adipate, maleate or sebacate of 1-(1-methyl-6-oxo-1,6-dihydropyridazin-3-yl)piperidin-4-yl 4-cyclobutylpiperazine-1-carboxylate. Unless specified otherwise, said free form or said salt together will be referred to hereinafter as "SOLID FORM OF THE INVENTION".

As used herein "solid form" may include hydrates and solvates.

As used herein "crystalline form" referes to a solid form of a molecule, atom and/or ion, in which its constituent atoms, molecules and/or ions are arranged in an orderly repeating pattern extending in all three spatial dimensions.

As used herein "polymorph" refers to crystalline forms having the same chemical composition but different spatial arrangements of the molecules, atoms and/or ions forming the crystal. As used herein "amorphous form" refers to a solid form of a molecule, atom and/or ion that is not crystalline. An amorphous solid does not display a definitive X-ray diffraction pattern. As used herein "solvate" refers to a form, e.g. a crystalline form, of a molecule, atom and/or ions that further comprises molecules of a solvent or solvents incorporated into the solid structure, e.g. crystalline lattice structure. The solvent molecules in the solvate may be present in a regular arrangement and/or a non-ordered arrangement. The solvate may comprise either a stoichiometic or nonstochiometric amount of the solvent molecules. For example, a solvate with a nonstochiometric amount of solvent molecules may result from partial loss of solvent form the solvate. Solvates may occur as dimers or oligomers comprising more than one molecule of 1-(1-methyl-6-oxo-1,6-dihydropyridazin-3-yl)piperidin-4-yl 4-cyclobutylpiperazine-1-carboxylate within a crystalline lattice structure.

As used herein "substantially pure", when used in reference to a solid form, means a compound, e.g. a salt (such as the citrate of 1-(1-methyl-6-oxo-1,6-dihydropyridazin-3-yl)piperidin-4-yl 4-cyclobutylpiperazine-1-carboxylate), having a purity greater than 90 weight %, including greater than 90, 91, 92, 93, 94, 95, 96, 97, 98, and 99 weight %, and also including equal to about 100 weight % of the compound, e.g. of the citrate of 1-(1-methyl-6-oxo-1,6-dihydropyridazin-3- yl)piperidin-4-yl 4-cyclobutylpiperazine-1-carboxylate, based on the weight of the solid form. The remaining material in the solid form may comprise e.g. reaction impurities and/or processing impurities arising from its preparation and/or—if applicable—other form(s) of the compound. For example, a crystalline form of the citrate of 1-(1-methyl-6-oxo-1,6-dihydropyridazin-3-yl)piperidin-4-yl 4-cyclobutylpiperazine-1-carboxylate may be deemed substantially pure in that it has a purity greater than 90 weight %, as measured by means that are at this time known and generally accepted in the art, where the remaining less than 10 weight % of material comprises reaction impurities and/or processing impurities.

As used herein "mono-" in connection with acids refers to a base to acid ratio of about 1:1.

As used herein "sesqui-" in connection with acids refers to a base to acid ratio of about 1:1.5.

As used herein "di-" in connection with acids refers to a base to acid ratio of about 1:2.

The term "substantially the same" with reference to X-ray diffraction peak positions means that typical peak position and intensity variability are taken into account. For example, one skilled in the art will appreciate that the peak positions (2θ) will show some inter-apparatus variability, typically as much as 0.2°. Further, one skilled in the art will appreciate that peak intensities will show inter-apparatus variability as well as variability due to degree of crystallinity, preferred orientation, prepared sample surface, and other factors known to those skilled in the art, and should be taken as qualitative measure only.

1. Free Form

In one embodiment, the SOLID FORM OF THE INVENTION is the free form of 1-(1-methyl-6-oxo-1,6-dihydropyridazin-3-yl)piperidin-4-yl 4-cyclobutylpiperazine-1-carboxylate, e.g. in crystalline form.

1.1. First Embodiment of Free Form:

A free form of 1-(1-methyl-6-oxo-1,6-dihydropyridazin-3-yl)piperidin-4-yl 4-cyclobutylpiperazine-1-carboxylate in crystalline form (Form A of the free form) may be produced from cooling crystallization of a supersaturated solution of the compound in ethyl acetate at concentrations of about 100 mg/ml. The clear point (temperature at which the compound will dissolve) is about 35° C. The cloud point (temperature at which the compound will crystallize) is about 4° C. The XRPD pattern of a sample prepared according to such a method (see also Example II.1.1) is shown in FIG. 1A. Measurements were performed at a temperature of about 22° C. and an x-ray wavelength, λ, of 1.5418 Å (CuKα λ=1.5418 Å).

Summary of XRPD Pattern:

| No. | 2 theta (deg°) | Intensity (cts) |
|---|---|---|
| 1 | 4.9 | 5305 |
| 2 | 9.7 | 2288 |
| 3 | 14.5 | 726 |
| 4 | 14.6 | 564 |
| 5 | 15.4 | 9230 |
| 6 | 16.0 | 3079 |
| 7 | 16.9 | 3327 |
| 8 | 17.3 | 1215 |
| 9 | 18.1 | 1995 |
| 10 | 19.5 | 2862 |
| 11 | 20.5 | 13826 |
| 12 | 20.8 | 8027 |
| 13 | 21.3 | 2578 |
| 14 | 21.4 | 2373 |
| 15 | 22.9 | 535 |
| 16 | 24.4 | 7248 |
| 17 | 24.8 | 918 |
| 18 | 26.0 | 400 |
| 19 | 26.8 | 799 |
| 20 | 28.8 | 460 |
| 21 | 29.4 | 1197 |
| 22 | 31.0 | 699 |
| 23 | 35.5 | 355 |
| 24 | 39.5 | 352 |

In one embodiment, Form A of the free form of 1-(1-methyl-6-oxo-1,6-dihydropyridazin-3-yl)piperidin-4-yl 4-cyclobutylpiperazine-1-carboxylate in crystalline form is characterized by an XRPD pattern with at least four, more preferably five, most preferably all of the following peaks at an angle of refraction 2 theta (2θ) of 4.9, 15.4, 16.9, 20.5, 20.8 and 24.4, ±0.2, respectively.

In one embodiment, Form A of the free form of 1-(1-methyl-6-oxo-1,6-dihydropyridazin-3-yl)piperidin-4-yl 4-cyclobutylpiperazine-1-carboxylate in crystalline form is characterized by an XRPD pattern substantially the same as the XRPD pattern shown in FIG. 1A.

Form A of the free from shows good solubility in aqueous media across a pH range from about 1-8. Its melting point was determined by heating at 10° C./minute to be about 123° C.

1.2. Second Embodiment of Free Form:

A free form of 1-(1-methyl-6-oxo-1,6-dihydropyridazin-3-yl)piperidin-4-yl 4-cyclobutylpiperazine-1-carboxylate in crystalline form (Form B of the free form) was found as described in the Examples section (see Example II.1.2). The associated XRPD pattern is shown in FIG. 1B.

Summary of XRPD Pattern:

| No. | 2 theta (deg°) | Intensity (cts) |
|---|---|---|
| 1 | 9.4 | 386 |
| 2 | 11.3 | 2380 |
| 3 | 13.6 | 348 |
| 4 | 15.0 | 2422 |
| 5 | 16.0 | 481 |
| 6 | 16.7 | 2577 |
| 7 | 17.4 | 1391 |
| 8 | 18.3 | 738 |
| 9 | 18.6 | 802 |
| 10 | 19.4 | 7589 |
| 11 | 20.8 | 1401 |
| 12 | 21.7 | 454 |
| 13 | 22.7 | 2907 |
| 14 | 23.2 | 7040 |
| 15 | 24.0 | 306 |
| 16 | 24.6 | 1591 |
| 17 | 27.7 | 10625 |
| 18 | 27.8 | 5756 |
| 19 | 28.1 | 712 |
| 20 | 28.7 | 1879 |
| 21 | 29.5 | 674 |
| 22 | 29.9 | 1086 |
| 23 | 31.6 | 637 |
| 24 | 32.5 | 1248 |
| 25 | 32.7 | 910 |
| 26 | 33.5 | 724 |
| 27 | 33.6 | 954 |
| 28 | 34.3 | 623 |
| 29 | 35.1 | 359 |
| 30 | 35.6 | 358 |
| 31 | 36.1 | 992 |
| 32 | 37.0 | 457 |
| 33 | 37.7 | 333 |
| 34 | 39.2 | 330 |

In one embodiment, Form B of the free form of 1-(1-methyl-6-oxo-1,6-dihydropyridazin-3-yl)piperidin-4-yl 4-cyclobutylpiperazine-1-carboxylate in crystalline form is characterized by an XRPD pattern with at least four, more preferably five, most preferably all of the following peaks at an angle of refraction 2 theta (2θ) of 9.4, 11.3, 13.6, 15.0, 16.0, 16.7, 17.4, 18.3, 18.6, 19.4, 20.8, 21.7, 22.7, 23.2, 24.0, 24.6, 27.7, 27.8, 28.1, 28.7, 29.5, 29.9, 31.6, 32.5, 32.7, 33.5, 33.6, 34.3, 35.1, 35.6, 36.1, 37.0, 37.7, and 39.2, ±0.2, respectively.

In one embodiment, Form B of the free form of 1-(1-methyl-6-oxo-1,6-dihydropyridazin-3-yl)piperidin-4-yl 4-cyclobutylpiperazine-1-carboxylate in crystalline form is characterized by an XRPD pattern with at least four, more preferably five, most preferably all of the following peaks at an angle of refraction 2 theta (2θ) of 9.4, 19.4, 22.7, 23.2, 27.7 and 27.8, ±0.2, respectively.

In one embodiment, Form B of the free form of 1-(1-methyl-6-oxo-1,6-dihydropyridazin-3-yl)piperidin-4-yl 4-cyclobutylpiperazine-1-carboxylate in crystalline form is characterized by an XRPD pattern substantially the same as the XRPD pattern shown in FIG. 1B.

Form B of the free from shows good solubility in aqueous media. Its melting point was determined by heating at 10° C./minute to be about 124° C. (onset).

Salts

2. Citrate Salt:

In one embodiment, the SOLID FORM OF THE INVENTION is the citrate salt of 1-(1-methyl-6-oxo-1,6-dihydropyridazin-3-yl)piperidin-4-yl 4-cyclobutylpiperazine-1-carboxylate, e.g. in crystalline form.

2.1. First Embodiment of Citrate Salt:

A citrate salt of 1-(1-methyl-6-oxo-1,6-dihydropyridazin-3-yl)piperidin-4-yl 4-cyclobutylpiperazine-1-carboxylate in crystalline form (Form A of the citrate salt) may be produced from acetone/diethylether when two equivalents citric acid are used.

It shows good solubility in aqueous media. Its melting point was determined by heating at 10° C./minute to be about 141.2° C.

The X-ray powder diffraction (XRPD) pattern of a sample prepared according to this method (see also Example II.2.1) is shown in FIG. 2A. Measurements were performed at a temperature of about 22° C. and an x-ray wavelength, λ, of 1.5418 Å (CuKα λ=1.5418 Å).

Summary of XRPD Pattern:

| No. | 2 theta (deg°) | Intensity |
|---|---|---|
| 1 | 19.4 | 130 |
| 2 | 24.0 | 130 |
| 3 | 14.0 | 128 |
| 4 | 16.6 | 128 |
| 5 | 17.5 | 128 |
| 6 | 17.3 | 122 |
| 7 | 12.0 | 118 |
| 8 | 20.8 | 110 |
| 9 | 25.6 | 108 |
| 10 | 16.1 | 103 |
| 11 | 22.5 | 103 |
| 12 | 18.2 | 99 |
| 13 | 20.1 | 97 |
| 14 | 10.2 | 93 |
| 15 | 31.3 | 82 |
| 16 | 8.4 | 60 |
| 17 | 5.5 | 57 |

In one embodiment, Form A of the citrate salt of 1-(1-methyl-6-oxo-1,6-dihydropyridazin-3-yl)piperidin-4-yl 4-cyclobutylpiperazine-1-carboxylate in crystalline form is characterized by an XRPD pattern with at least four, more preferably five, most preferably all of the following peaks at an angle of refraction 2 theta (2θ) of 14.0, 16.6, 17.3, 17.5, 19.4 and 24.0 ±0.2, respectively.

In one embodiment, Form A of the citrate salt of 1-(1-methyl-6-oxo-1,6-dihydropyridazin-3-yl)piperidin-4-yl 4-cyclobutylpiperazine-1-carboxylate in crystalline form is characterized by an XRPD pattern substantially the same as the XRPD pattern shown in FIG. 2A.

Analysis of the proton-NMR spectrum for the salt of Example II.2.1 (see FIG. 2B) demonstrated a base/acid ratio of about 1:1.5.

In one embodiment, the SOLID FORM OF THE INVENTION is the sesqui-citrate salt of 1-(1-methyl-6-oxo-1,6-dihydropyridazin-3-yl)piperidin-4-yl 4-cyclobutylpiperazine-1-carboxylate.

In one embodiment, the SOLID FORM OF THE INVENTION is the sesqui-citrate salt of 1-(1-methyl-6-oxo-1,6-dihydropyridazin-3-yl)piperidin-4-yl 4-cyclobutylpiperazine-1-carboxylate in crystalline form.

2.2. Second Embodiment of Citrate Salt:

A citrate salt of 1-(1-methyl-6-oxo-1,6-dihydropyridazin-3-yl)piperidin-4-yl 4-cyclobutylpiperazine-1-carboxylate in crystalline form (Form B of the citrate salt) may be produced from acetone when one equivalent citric acid is used.

It shows good solubility in aqueous media. Its melting point was determined by heating at 10° C./minute to be about 172° C.

The X-ray powder diffraction (XRPD) pattern of a sample prepared according to this method (see also Example II.2.2) is shown in FIG. 2C. The sample contained about 1.5% of residual acetone. Measurements were performed at a temperature of about 22° C. and an x-ray wavelength, λ, of 1.5418 Å (CuKα λ=1.5418 Å).

Summary of XRPD Pattern:

| No. | 2 theta (deg°) | Intensity (cts) |
|---|---|---|
| 1 | 3.2 | 406 |
| 2 | 5.8 | 54 |
| 3 | 9.3 | 1460 |
| 4 | 10.8 | 321 |
| 5 | 12.0 | 1561 |
| 6 | 12.7 | 134 |
| 7 | 14.1 | 110 |
| 8 | 15.1 | 204 |
| 9 | 16.3 | 811 |
| 10 | 16.4 | 772 |
| 11 | 17.3 | 1164 |
| 12 | 18.3 | 437 |
| 13 | 18.6 | 406 |
| 14 | 19.3 | 425 |
| 15 | 20.7 | 469 |
| 16 | 22.0 | 97 |
| 17 | 23.3 | 271 |
| 18 | 23.9 | 308 |
| 19 | 25.9 | 138 |
| 20 | 26.7 | 98 |
| 21 | 27.9 | 38 |
| 22 | 31.0 | 27 |
| 23 | 31.7 | 35 |
| 24 | 32.5 | 50 |
| 25 | 34.9 | 60 |
| 26 | 37.2 | 65 |

In one embodiment, Form B of the citrate salt of 1-(1-methyl-6-oxo-1,6-dihydropyridazin-3-yl)piperidin-4-yl 4-cyclobutylpiperazine-1-carboxylate in crystalline form is characterized by an XRPD pattern with at least four, more preferably five, most preferably all of the following peaks at an angle of refraction 2 theta (2θ) of 3.2, 9.3, 10.8, 12.0, 15.1, 16.3, 16.4, 17.3, 18.3, 18.6, 19.3, 20.7, 23.3, and 23.9, ±0.2, respectively.

In one embodiment, Form B of the citrate salt of 1-(1-methyl-6-oxo-1,6-dihydropyridazin-3-yl)piperidin-4-yl 4-cyclobutylpiperazine-1-carboxylate in crystalline form is characterized by an XRPD pattern substantially the same as the XRPD pattern shown in FIG. 2C.

3. Hydrochloride Salt:

In one embodiment, the SOLID FORM OF THE INVENTION is the hydrochloride salt of 1-(1-methyl-6-oxo-1,6-dihydropyridazin-3-yl)piperidin-4-yl 4-cyclobutylpiperazine-1-carboxylate, e.g. in crystalline form.

4.1. First Embodiment of Hydrochloride Salt:

A hydrochloride salt of 1-(1-methyl-6-oxo-1,6-dihydropyridazin-3-yl)piperidin-4-yl 4-cyclobutylpiperazine-1-carboxylate in crystalline form (Form A of hydrochloride salt) may be produced from acetone when one equivalent hydrochloric acid is used.

It shows good solubility in aqueous media. Its melting point was determined by heating at 10° C./minute to be 249.8° C. (onset) with subsequent decomposition.

The XRPD pattern pattern of a sample prepared according to this method (see also Example II.3.1) is shown in FIG. 3A. Measurements were performed at a temperature of about 22° C. and an x-ray wavelength, λ, of 1.5418 Å (CuKα λ=1.5418 Å).

Summary of XRPD Pattern:

| No. | 2 theta (deg°) | Intensity |
|---|---|---|
| 1 | 16.4 | 287 |
| 2 | 24.8 | 215 |
| 3 | 27.5 | 153 |
| 4 | 20.2 | 119 |
| 5 | 29.7 | 103 |
| 6 | 17.2 | 96 |
| 7 | 27.0 | 94 |
| 8 | 22.0 | 91 |
| 9 | 19.0 | 82 |
| 10 | 23.9 | 81 |
| 11 | 10.9 | 77 |
| 12 | 36.4 | 68 |
| 13 | 39.0 | 66 |
| 14 | 14.0 | 59 |
| 15 | 31.2 | 56 |
| 16 | 43.6 | 38 |
| 17 | 40.5 | 37 |

In one embodiment, Form A of the hydrochloride salt of 1-(1-methyl-6-oxo-1,6-dihydropyridazin-3-yl)piperidin-4-yl 4-cyclobutylpiperazine-1-carboxylate in crystalline form is characterized by an XRPD pattern with at least four, more preferably five, most preferably all of the following peaks at an angle of refraction 2 theta (2θ) of 16.4, 17.2, 20.2, 24.2, 27.5 and 29.7±0.2, respectively.

In one embodiment, Form A of the hydrochloride salt of 1-(1-methyl-6-oxo-1,6-dihydropyridazin-3-yl)piperidin-4-yl 4-cyclobutylpiperazine-1-carboxylate in crystalline form is characterized by an XRPD pattern substantially the same as the XRPD pattern shown in FIG. 3A.

4.2. Second Embodiment of Hydrochloride Salt:

An anhydrous hydrochloride salt of 1-(1-methyl-6-oxo-1,6-dihydropyridazin-3-yl)piperidin-4-yl 4-cyclobutylpiperazine-1-carboxylate in crystalline form (Form B of hydrochloride salt) may be produced from acetone when two equivalents hydrochloric acid are used.

It shows good solubility in aqueous media. Its melting point, for a sample stored at 40° C. and 75% relative umidity for 7 days, was determined by heating at 10° C./minute to be about 250° C. (onset).

The X-ray powder diffraction (XRPD) pattern of a sample prepared according to this method (see also Example II.3.2) is shown in FIG. 3B. Measurements were performed at a temperature of about 22° C. and an x-ray wavelength, λ, of 1.5418 Å (CuKα λ=1.5418 Å).

Summary of XRPD Pattern:

| No. | 2 theta (deg°) | Intensity (cts) |
|---|---|---|
| 1 | 5.7 | 98 |
| 2 | 9.1 | 76 |
| 3 | 10.0 | 603 |
| 4 | 10.7 | 521 |
| 5 | 11.9 | 463 |
| 6 | 13.3 | 418 |
| 7 | 13.7 | 163 |
| 8 | 15.4 | 191 |
| 9 | 15.9 | 970 |
| 10 | 16.5 | 225 |
| 11 | 16.8 | 127 |
| 12 | 17.1 | 135 |
| 13 | 18.3 | 494 |
| 14 | 18.7 | 443 |
| 15 | 19.5 | 439 |
| 16 | 20.0 | 80 |
| 17 | 20.7 | 82 |
| 18 | 22.9 | 36 |
| 19 | 23.6 | 323 |
| 20 | 24.2 | 136 |
| 21 | 25.0 | 595 |
| 22 | 25.4 | 137 |
| 23 | 26.9 | 1100 |
| 24 | 27.0 | 966 |
| 25 | 27.7 | 296 |
| 26 | 29.4 | 198 |
| 27 | 30.1 | 67 |
| 28 | 31.9 | 51 |
| 29 | 32.7 | 63 |
| 30 | 34.2 | 20 |
| 31 | 35.9 | 30 |
| 32 | 38.1 | 22 |

In one embodiment, Form B of the hydrochloride salt of 1-(1-methyl-6-oxo-1,6-dihydropyridazin-3-yl)piperidin-4-yl 4-cyclobutylpiperazine-1-carboxylate in crystalline form is characterized by an XRPD pattern with at least four, more preferably five, most preferably all of the following peaks at an angle of refraction 2 theta (2θ) of 5.7, 9.1, 10.0, 10.7, 11.9, 13.3, 13.7, 15.4, 15.9, 16.5, 16.8, 17.1, 18.3, 18.7, 19.5, 20.0, 20.7, 23.6, 24.2, 25.0, 25.4, 26.9, 27.0, 27.7, 29.4, 30.1, 31.9, and 32.7, ±0.2, respectively.

In one embodiment, Form B of the hydrochloride salt of 1-(1-methyl-6-oxo-1,6-dihydropyridazin-3-yl)piperidin-4-yl 4-cyclobutylpiperazine-1-carboxylate in crystalline form is characterized by an XRPD pattern substantially the same as the XRPD pattern shown in FIG. 3B.

4. Fumarate Salt:

In one embodiment, the SOLID FORM OF THE INVENTION is the fumarate salt of 1-(1-methyl-6-oxo-1,6-dihydropyridazin-3-yl)piperidin-4-yl 4-cyclobutylpiperazine-1-carboxylate, e.g. in crystalline form.

3.1. First Embodiment of Fumarate Salt:

An anhydrous fumarate salt of 1-(1-methyl-6-oxo-1,6-dihydropyridazin-3-yl)piperidin-4-yl 4-cyclobutylpiperazine-1-carboxylate in crystalline form (Form A of fumarate salt)

may be produced from methanol/acetone as described in Example 4.1 when one equivalent fumaric acid is used.

It shows good solubility in aqueous media. Its melting point was determined by heating at 10° C./minute to be about 156° C.

The X-ray powder diffraction (XRPD) pattern of a sample prepared according to this method (see also Example II.4.1) is shown in FIG. 4A. Measurements were performed at a temperature of about 22° C. and an x-ray wavelength, λ, of 1.5418 Å (CuKα λ=1.5418 Å).
Summary of XRPD Pattern:

| No. | 2 theta (deg°) | Intensity (cts) |
|---|---|---|
| 1 | 6.5 | 662 |
| 2 | 10.1 | 1209 |
| 3 | 10.7 | 813 |
| 4 | 12.4 | 156 |
| 5 | 13.0 | 3669 |
| 6 | 13.9 | 661 |
| 7 | 16.0 | 90 |
| 8 | 16.7 | 1428 |
| 9 | 16.8 | 1725 |
| 10 | 17.2 | 2712 |
| 11 | 17.7 | 290 |
| 12 | 18.8 | 209 |
| 13 | 20.2 | 1475 |
| 14 | 20.5 | 631 |
| 15 | 21.6 | 1518 |
| 16 | 21.9 | 1748 |
| 17 | 22.1 | 1795 |
| 18 | 23.1 | 237 |
| 19 | 23.4 | 100 |
| 20 | 25.0 | 1464 |
| 21 | 25.1 | 1002 |
| 22 | 25.4 | 603 |
| 23 | 26.4 | 114 |
| 24 | 27.5 | 297 |
| 25 | 28.0 | 790 |
| 26 | 28.8 | 293 |
| 27 | 29.9 | 255 |
| 28 | 32.8 | 149 |
| 29 | 33.2 | 174 |
| 30 | 33.7 | 80 |
| 31 | 38.3 | 73 |

In one embodiment, Form A of the fumarate salt of 1-(1-methyl-6-oxo-1,6-dihydropyridazin-3-yl)piperidin-4-yl 4-cyclobutylpiperazine-1-carboxylate in crystalline form is characterized by an XRPD pattern with at least four, more preferably five, most preferably all of the following peaks at an angle of refraction 2 theta (2θ) of 6.5, 10.1, 10.7, 12.4, 13.0, 13.9, 16.7, 16.8, 17.2, 17.7, 18.8, 20.2, 20.5, 21.6, 21.9, 22.1, 23.1, 23.4, 25.0, 25.1, 25.4, 26.4, 27.5, 28.0, 28.8, 29.9, 32.8, and 33.2, ±0.2, respectively.

In one embodiment, Form A of the fumarate salt of 1-(1-methyl-6-oxo-1,6-dihydropyridazin-3-yl)piperidin-4-yl 4-cyclobutylpiperazine-1-carboxylate in crystalline form is characterized by an XRPD pattern substantially the same as the XRPD pattern shown in FIG. 4A.

3.2. Second Embodiment of Fumarate Salt:

An anhydrous fumarate salt of 1-(1-methyl-6-oxo-1,6-dihydropyridazin-3-yl)piperidin-4-yl 4-cyclobutylpiperazine-1-carboxylate in crystalline form (Form B of fumarate salt) may be produced from methanol/acetone as described in Example 4.2 when two equivalents fumaric acid are used.

It shows good solubility in aqueous media. Its melting point was determined by heating at 10° C./minute to be about 155° C.

The X-ray powder diffraction (XRPD) pattern of a sample prepared according to this method (see also Example II.4.2) is shown in FIG. 4B. Measurements were performed at a temperature of about 22° C. and an x-ray wavelength, λ, of 1.5418 Å (CuKα λ=1.5418 Å).
Summary of XRPD Pattern:

| No. | 2 theta (deg°) | Intensity (cts) |
|---|---|---|
| 1 | 6.4 | 549 |
| 2 | 7.8 | 112 |
| 3 | 8.7 | 462 |
| 4 | 10.6 | 232 |
| 5 | 11.3 | 215 |
| 6 | 11.8 | 742 |
| 7 | 12.9 | 523 |
| 8 | 13.1 | 178 |
| 9 | 13.8 | 1953 |
| 10 | 14.0 | 1727 |
| 11 | 15.2 | 176 |
| 12 | 15.7 | 1780 |
| 13 | 16.2 | 736 |
| 14 | 16.6 | 1901 |
| 15 | 16.9 | 335 |
| 16 | 18.3 | 110 |
| 17 | 18.7 | 954 |
| 18 | 18.8 | 689 |
| 19 | 19.1 | 2404 |
| 20 | 19.3 | 562 |
| 21 | 19.7 | 318 |
| 22 | 20.1 | 146 |
| 23 | 20.5 | 323 |
| 24 | 21.0 | 1741 |
| 25 | 21.4 | 840 |
| 26 | 21.9 | 2681 |
| 27 | 22.8 | 669 |
| 28 | 23.8 | 364 |
| 29 | 24.0 | 1027 |
| 30 | 24.4 | 317 |
| 31 | 24.7 | 524 |
| 32 | 25.2 | 935 |
| 33 | 25.6 | 448 |
| 34 | 26.0 | 566 |
| 35 | 26.1 | 699 |
| 36 | 27.8 | 528 |
| 37 | 28.3 | 123 |
| 38 | 29.1 | 220 |
| 39 | 29.5 | 353 |
| 40 | 30.6 | 201 |
| 41 | 31.4 | 256 |
| 42 | 31.7 | 142 |
| 43 | 32.1 | 318 |
| 44 | 32.7 | 308 |
| 45 | 34.7 | 98 |
| 46 | 35.3 | 194 |
| 47 | 37.4 | 154 |
| 48 | 38.2 | 168 |

In one embodiment, Form B of the fumarate salt of 1-(1-methyl-6-oxo-1,6-dihydropyridazin-3-yl)piperidin-4-yl 4-cyclobutylpiperazine-1-carboxylate in crystalline form is characterized by an XRPD pattern with at least four, more preferably five, most preferably all of the following peaks at an angle of refraction 2 theta (2θ) of 6.4, 8.7, 10.6, 11.3, 11.8, 12.9, 13.8, 14.0, 15.7, 16.2, 16.6, 16.9, 18.7, 18.8, 19.1, 19.3, 19.7, 20.5, 21.0, 21.4, 21.9, 22.8, 23.8, 24.0, 24.4, 24.7, 25.2, 25.6, 26.0, 26.1, 27.8, 29.1, 29.5, 30.6, 31.4, 32.1, 32.7, and 35.3, ±0.2, respectively.

In one embodiment, Form B of the fumarate salt of 1-(1-methyl-6-oxo-1,6-dihydropyridazin-3-yl)piperidin-4-yl 4-cyclobutylpiperazine-1-carboxylate in crystalline form is characterized by an XRPD pattern substantially the same as the XRPD pattern shown in FIG. 4B.

Preparation Methods for Crystalline Forms

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in Solid-State Chemistry of Drugs, S. R. Byrn, R. R. Pfeiffer, and J. G. Stowell, $2^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization (see "Programmed Cooling of Batch Crystallizers," J. W. Mullin and J. Nyvlt, *Chemical Engineering Science*, 1971,26, 369-377). In general, seed crystals of small size are used. Seed crystals of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be delumped by sieving or forced sieving, if necessary.

Crystalline forms may be prepared directly from the reaction medium of the final process for preparing 1-(1-methyl-6-oxo-1,6-dihydropyridazin-3-yl)piperidin-4-yl 4-cyclobutylpiperazine-1-carboxylate or a SOLID FORM OF THE INVENTION. This may be achieved, for example, by employing in the final process step a solvent or a mixture of solvents from which the SOLID FORM OF THE INVENTION may be crystallized. Alternatively, crystalline forms may be obtained by distillation or solvent addition techniques. Suitable solvents for this purpose include, for example, nonpolar solvents and polar solvents, including protic polar solvents such as alcohols, and aprotic polar solvents such as ketones.

The presence of more than one polymorph in a sample may be determined by techniques such as powder x-ray diffraction (PXRD) or solid state nuclear magnetic resonance spectroscopy. For example, the presence of extra peaks in the comparison of an experimentally measured PXRD pattern with a simulated PXRD pattern may indicate more than one polymorph in the sample. The simulated PXRD may be calculated from single crystal x-ray data; see Smith, D. K., "*A FORTRAN Program for Calculating X-Ray Powder Diffraction Patterns*," Lawrence Radiation Laboratory, Livermore, Calif., UCRL-7196 (April 1963).

One embodiment of the invention is a method of preparing a citrate salt of 1-(1-methyl-6-oxo-1,6-dihydropyridazin-3-yl)piperidin-4-yl 4-cyclobutylpiperazine-1-carboxylate in crystalline form comprising the steps of (a) preparing a solution of 1-(1-methyl-6-oxo-1,6-dihydropyridazin-3-yl)piperidin-4-yl 4-cyclobutylpiperazine-1-carboxylate and citric acid in acetone, wherein the 1-(1-methyl-6-oxo-1,6-dihydropyridazin-3-yl)piperidin-4-yl 4-cyclobutylpiperazine-1-carboxylate:citric acid ratio is about 1:2;

(b) adding to the solution of step (a) an ether antisolvent, e.g. diethyl ether, until an acetone:ether antisolvent volume ratio from 1:1 to 1:5, e.g. about 1:3, is reached; and (e) isolate the solids by filtration to obtain the citrate salt of 1-(1-methyl-6-oxo-1,6-dihydropyridazin-3-yl)piperidin-4-yl 4-cyclobutylpiperazine-1-carboxylate in crystalline form.

One embodiment of the invention is a method of preparing a hydrochloride salt of 1-(1-methyl-6-oxo-1,6-dihydropyridazin-3-yl)piperidin-4-yl 4-cyclobutylpiperazine-1-carboxylate in crystalline form comprising the steps of (a) preparing a solution of 1-(1-methyl-6-oxo-1,6-dihydropyridazin-3-yl)piperidin-4-yl 4-cyclobutylpiperazine-1-carboxylate in acetone;

(b) adding to the solution of step (a) hydrochloric acid until a 1-(1-methyl-6-oxo-1,6-dihydropyridazin-3-yl)piperidin-4-yl 4-cyclobutylpiperazine-1-carboxylate:hydrochloric acid ratio of about 1:1 is reached; and (e) isolate the solids by filtration to obtain the hydrochloride salt of 1-(1-methyl-6-oxo-1,6-dihydropyridazin-3-yl)piperidin-4-yl 4-cyclobutylpiperazine-1-carboxylate in crystalline form.

Analysis of Solid Forms

The solid form of a SOLID FORM OF THE INVENTION may be characterized using various techniques, the operation of which are well known to those of ordinary skill in the art.

The forms may be characterized and distinguished using single crystal x-ray diffraction, which is based on unit cell measurements of a single crystal of the form at a fixed analytical temperature. A detailed description of unit cells is provided in Stout & Jensen, X-Ray Structure Determination: A Practical Guide, Macmillan Co., New York (1968), Chapter 3. Alternatively, the unique arrangement of atoms in spatial relation within the crystalline lattice may be characterized according to the observed fractional atomic coordinates. Another means of characterizing the crystalline structure is by powder x-ray diffraction analysis in which the diffraction profile is compared to a simulated profile representing pure powder material, both run at the same analytical temperature, and measurements for the subject form characterized as a series of 2θ values (usually four or more).

Other means of characterizing the form may be used, such as solid state nuclear magnetic resonance (NMR), differential scanning calorimetry, thermography and gross examination of the crystalline or amorphous morphology. These parameters may also be used in combination to characterize the subject form.

Further Aspects

The invention also relates to a SOLID FORM OF THE INVENTION (e.g. Form A of the free form of 1-(1-methyl-6-oxo-1,6-dihydropyridazin-3-yl)piperidin-4-yl 4-cyclobutylpiperazine-1-carboxylate in crystalline form) for use as a medicament.

In another embodiment, the invention relates to a SOLID FORM OF THE INVENTION (e.g. Form A of the free form of 1-(1-methyl-6-oxo-1,6-dihydropyridazin-3-yl)piperidin-4-yl 4-cyclobutylpiperazine-1-carboxylate in crystalline form) for the treatment of a disorder or disease in a subject mediated by H3 receptors. Preferably said disorder or said disease is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

In another embodiment, the invention also relates to the use of a SOLID FORM OF THE INVENTION (e.g. Form A of the free form of 1-(1-methyl-6-oxo-1,6-dihydropyridazin-3-yl)piperidin-4-yl 4-cyclobutylpiperazine-1-carboxylate in crystalline form) for the manufacture of a medicament for the prevention, treatment and/or delay of progression of a disorder or disease in a subject mediated by H3 receptors. Preferably said disorder or said disease is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

In another embodiment, the invention also relates to the use of a SOLID FORM OF THE INVENTION (e.g. Form A of the free form of 1-(1-methyl-6-oxo-1,6-dihydropyridazin-3-yl)piperidin-4-yl 4-cyclobutylpiperazine-1-carboxylate in crystalline form) for the prevention, treatment and/or delay of progression of a disorder or disease in a subject mediated by H3 receptors. Preferably said disorder or said disease is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

In another embodiment, the invention also relates to a method for the prevention, treatment and/or delay of progression of a disorder or disease in a subject mediated by H3 receptors, in a subject in need of such treatment, which comprises administering to such subject a therapeutically effective amount of a SOLID FORM OF THE INVENTION (e.g. Form A of the free form of 1-(1-methyl-6-oxo-1,6-dihydropyridazin-3-yl)piperidin-4-yl 4-cyclobutylpiperazine-1-carboxylate in crystalline form). Preferably said disorder or said disease is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

In another embodiment, the invention relates to a method for the prevention, treatment and/or delay of progression of a disorder or disease in a subject mediated by H3 receptors, in a subject in need thereof, which comprises (i) diagnosing said disorder or disease in said subject and (ii) administering to said subject a therapeutically effective amount of a SOLID FORM OF THE INVENTION (e.g. Form A of the free form of 1-(1-methyl-6-oxo-1,6-dihydropyridazin-3-yl)piperidin-4-yl 4-cyclobutylpiperazine-1-carboxylate in crystalline form). Preferably said disorder or said disease is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

Amorphous forms/crystalline forms of SOLID FORMS OF THE INVENTION are useful as intermediates for preparing crystalline forms/other crystalline forms of SOLID FORMS OF THE INVENTION that are useful in the treatment of the above diseases/conditions.

SOLID FORMS OF THE INVENTION may be used alone or in combination, or formulated with one or more excipients and/or other active pharmaceutical ingredients to provide formulations, as described above, suitable for the treatment of the above diseases/conditions.

The invention therefore also relates to a pharmaceutical composition comprising a SOLID FORM OF THE INVENTION as active ingredient and at least one pharmaceutically acceptable carrier.

Abbreviations:
DSC Differential scanning calorimetry
EGA evolved gas analysis
TGA thermo gravimetric analysis
XRPD X-ray powder diffraction Example II.1.1

Preparation of Free Form of 1-(1-methyl-6-oxo-1,6-dihydropyridazin-3-yl)piperidin-4-yl 4-cyclobutylpiperazine-1-carboxylate in Crystalline Form Free form of 1-(1-methyl-6-oxo-1,6-dihydropyridazin-3-yl)piperidin-4-yl 4-cyclobutylpiperazine-1-carboxylate was dissolved in ethyl acetate at a concentration of 100 mg/ml under heating to its clear point of 35° C. Cooling to its cloud point of 4° C. yielded a crystalline product. The product was analyzed by XRPD (see FIG. 1A).

Example II.1.2

Preparation of Free Form of 1-(1-methyl-6-oxo-1,6-dihydropyridazin-3-yl)piperidin-4-yl 4-cyclobutylpiperazine-1-carboxylate in Crystalline Form In a vial, equipped with a magnetic stirring bar, 1 equivalent of each base listed in the table below was dissolved in 3 ml water. To this solution, 50 mg Form A of the free form of 1-(1-methyl-6-oxo-1,6-dihydropyridazin-3-yl)piperidin-4-yl 4-cyclobutylpiperazine-1-carboxylate were added together with 2 ml methanol. The mixture was stirred at room temperature until a clear solution was obtained. Then, the stirring bar was removed and the solution was left to evaporate at room temperature. After 17-24 days (see table below), a crystalline product was obtained. The evaporation time and the amount of product obtained are listed below:

| Base | Amount of product | Evaporation time |
| --- | --- | --- |
| L-Lysine | 19 mg | 17 days |
| N-Methyl Glucamine | 26 mg | 24 days |
| L-Arginine | 23 mg | 18 days |
| Sodium Hydroxide | 5 mg | 20 days |
| Potassium Hydroxide | 7 mg | 24 days |
| Magnesium Hydroxide | 8 mg | 18 days |
| Calcium Hydroxide | 10 mg | 24 days |

Precipitates were collected and analyzed by XRPD. A typical XRPD spectrum is depicted in FIG. 1B.

Example II2.1

Preparation of Citrate Salt of 1-(1-methyl-6-oxo-1,6-dihydropyridazin-3-yl)piperidin-4-yl 4-cyclobutylpiperazine-1-carboxylate in Crystalline Form 2 g free form of 1-(1-methyl-6-oxo-1,6-dihydropyridazin-3-yl)piperidin-4-yl 4-cyclobutylpiperazine-1-carboxylate was dissolved in acetone (5 ml) under stirring at room temperature, and 2.04 g (2 equivalents) of citric acid was also dissolved in acetone (5 ml) in the same condition. In a 100 ml crystallizer, equipped with a magnetic stirring bar and condenser, two solutions were added and stirred. After half an hour, 30 ml diethyl ether was added into crystallizer. The slurry was filtered, and the light yellow solid was dried under vacuum at 40° C. for 24 hours (yield: 82.28%). The product was analyzed by XRPD (see FIG. 2A) and proton-NMR (see FIG. 2B). Analysis of the proton-NMR spectrum demonstrated a base/acid ratio of about 1:1.5.

Example II.2.2

Preparation of Citrate Salt of 1-(1-methyl-6-oxo-1,6-dihydropyridazin-3-yl)piperidin-4-yl 4-cyclobutylpiperazine-1-carboxylate in Crystalline Form 25.58 mg of citric acid was dissolved in 3 ml acetone under stirring until complete dissolution. 50 mg free form of 1-(1-methyl-6-oxo-1,6-dihydropyridazin-3-yl)piperidin-4-yl 4-cyclobutylpiperazine-1-carboxylate was added to the solution and the mixture was stirred at room temperature for 24 hours. The precipitate was collected by vacuum filtration, washed with diethyl ether, dried under vacuum at 50° C. for 14 hours and analyzed by XRPD (see FIG. 2B), TGA/EGA and DSC.

Example II.3.1

Preparation of Hydrochloride Salt of 1-(1-methyl-6-oxo-1,6-dihydropyridazin-3-yl)piperidin-4-yl 4-cyclobutylpiperazine-1-carboxylate in Crystalline Form In a 100 ml crystallizer, equipped with a magnetic stirring bar and condenser, 2 g free form of 1-(1-methyl-6-oxo-1,6-dihydropyridazin-3-yl)piperidin-4-yl 4-cyclobutylpiperazine-1-carboxylate was dissolved in acetone under stirring. At room temperature 438 µl (1 equivalent) of hydrochloric acid was added drop wise. A slight yellow precipitate was immediately formed, and the mixture was stirred at room temperature for 3 hours. The solid was filtered, dried under vacuum at 40° C. for 24 hours (yield: 81.5%) and analyzed by XRPD (see FIG. 3A).

Example II.3.2

Preparation of Hydrochloride Salt of 1-(1-methyl-6-oxo-1,6-dihydropyridazin-3-yl)piperidin-4-yl 4-cyclobutylpiperazine-1-carboxylate in Crystalline Form 50 mg of free form of 1-(1-methyl-6-oxo-1,6-dihydropyridazin-3-yl)piperidin-4-yl 4-cyclobutylpiperazine-1-carboxylate was dissolved in 3 ml acetone. At room temperature, 22 µl of 37% hydrochloric acid was added and the mixture was stirred at room temperature for 24 hours. The precipitate was recovered under vacuum, washed with diethyl ether, dried under vacuum at 50° C. for 24 hours, and analyzed by XRPD (see FIG. 3B), TGA/EGA and DSC.

Example II.4.1

Preparation of Fumarate Salt of 1-(1-methyl-6-oxo-1,6-dihydropyridazin-3-yl)piperidin-4-yl 4-cyclobutylpiperazine-1-carboxylate in Crystalline Form 15.46 mg of fumaric acid was dissolved in 1 ml methanol under stirring until complete dissolution. 50 mg free form of 1-(1-methyl-6-oxo-1,6-dihydropyridazin-3-yl)piperidin-4-yl 4-cyclobutylpiperazine-1-carboxylate was added to the solution and the mixture was stirred at room temperature until complete dissolution. The solvents were evaporated at room temperature for 48 hours and a yellow oil was obtained. 1 ml acetone was added and the mixture stirred stirred at room temperature for 2 hours. A yellow precipitate was recovered under vacuum, washed with diethyl ether, dried under vacuum at 50° C. for 14 hours, and analyzed by XRPD (see FIG. 4A), TGA/EGA and DSC.

Example II.4.2

Preparation of Fumarate Salt of 1-(1-methyl-6-oxo-1,6-dihydropyridazin-3-yl)piperidin-4-yl 4-cyclobutylpiperazine-1-carboxylate in Crystalline Form 30.91 mg of fumaric acid was dissolved in 2 ml methanol under stirring until complete dissolution. 50 mg free form of 1-(1-methyl-6-oxo-1,6-dihydropyridazin-3-yl)piperidin-4-yl 4-cyclobutylpiperazine-1-carboxylate was added to the solution and the mixture was stirred at room temperature until complete dissolution. The solvents were evaporated at room temperature for 3 days and a yellow oil was obtained. 1 ml acetone was added and the mixture stirred stirred at room temperature for 2 hours. A yellow precipitate was recovered under vacuum, washed with diethyl ether, dried under vacuum at 50° C. for 14 hours, and analyzed by XRPD (see FIG. 4A), TGA/EGA and DSC.

The following are further embodiments of the invention:

Embodiment 1

A free form of 1-(1-methyl-6-oxo-1,6-dihydropyridazin-3-yl)piperidin-4-yl 4-cyclobutylpiperazine-1-carboxylate in solid form; or a salt of 1-(1-methyl-6-oxo-1,6-dihydropyridazin-3-yl)piperidin-4-yl 4-cyclobutylpiperazine-1-carboxylate in solid form, wherein said salt is the citrate, hydrochloride, fumarate, adipate, maleate or sebacate of 1-(1-methyl-6-oxo-1,6-dihydropyridazin-3-yl)piperidin-4-yl 4-cyclobutylpiperazine-1-carboxylate.

Embodiment 2

A free form of 1-(1-methyl-6-oxo-1,6-dihydropyridazin-3-yl)piperidin-4-yl 4-cyclobutylpiperazine-1-carboxylate in solid form.

Embodiment 3

The free form according to embodiment 2, wherein the free form is in crystalline form.

Embodiment 4

The free form according to embodiment 3, wherein the free form is characterized by an XRPD pattern substantially the same as the XRPD pattern shown in FIG. 1A.

Embodiment 5

The free form according to any one of embodiments 2 to 4, wherein the free form is in substantially pure form.

Embodiment 6

The free form according to any one of embodiments 2 to 4, wherein the free form has a purity greater than 90 weight %.

Embodiment 7

A salt of 1-(1-methyl-6-oxo-1,6-dihydropyridazin-3-yl)piperidin-4-yl 4-cyclobutylpiperazine-1-carboxylate in solid form, wherein said salt is the citrate, hydrochloride, fumarate, adipate, maleate or sebacate of 1-(1-methyl-6-oxo-1,6-dihydropyridazin-3-yl)piperidin-4-yl 4-cyclobutylpiperazine-1-carboxylate.

Embodiment 8

The salt according to embodiment 7, wherein the salt is the citrate of 1-(1-methyl-6-oxo-1,6-dihydropyridazin-3-yl)piperidin-4-yl 4-cyclobutylpiperazine-1-carboxylate in crystalline form.

Embodiment 9

The salt according to embodiment 8, wherein the salt is characterized by an XRPD pattern substantially the same as the XRPD pattern shown in FIG. 2A.

Embodiment 10

The salt according to any one of embodiments 7 to 9, wherein the salt is in substantially pure form.

Embodiment 11

The salt according to any one of embodiments 7 to 9, wherein the salt has a purity greater than 90 weight %.

Embodiment 12

A pharmaceutical composition, which comprises a free form as defined in any one of embodiments 2 to 6 as active ingredient and at least one pharmaceutically acceptable carrier.

Embodiment 13

A pharmaceutical composition, which comprises a salt as defined in any one of claims 7 to 11 as active ingredient and at least one pharmaceutically acceptable carrier.

Embodiment 14

A method of preparing a citrate salt of 1-(1-methyl-6-oxo-1,6-dihydropyridazin-3-yl)piperidin-4-yl 4-cyclobutylpiperazine-1-carboxylate in crystalline form comprising the steps of (a) preparing a solution of 1-(1-methyl-6-oxo-1,6-dihydropyridazin-3-yl)piperidin-4-yl 4-cyclobutylpiperazine-1-carboxylate and citric acid in acetone, wherein the 1-(1-methyl-6-oxo-1,6-dihydropyridazin-3-yl)piperidin-4-yl 4-cyclobutylpiperazine-1-carboxylate:citric acid ratio is about 1:2;

(b) adding to the solution of step (a) an ether antisolvent, e.g. diethyl ether, until an acetone:ether antisolvent volume ratio from 1:1 to 1:5 is reached; and (e) isolate the solids by filtration to obtain the citrate salt of 1-(1-methyl-6-oxo-1,6-dihydropyridazin-3-yl)piperidin-4-yl 4-cyclobutylpiperazine-1-carboxylate in crystalline form.

Embodiment 15

A method of preparing a hydrochloride salt of 1-(1-methyl-6-oxo-1,6-dihydropyridazin-3-yl)piperidin-4-yl 4-cyclobutylpiperazine-1-carboxylate in crystalline form comprising the steps of (a) preparing a solution of 1-(1-methyl-6-oxo-1,6-dihydropyridazin-3-yl)piperidin-4-yl 4-cyclobutylpiperazine-1-carboxylate in acetone;

(b) adding to the solution of step (a) hydrochloric acid until a 1-(1-methyl-6-oxo-1,6-dihydropyridazin-3-yl)piperidin-4-yl 4-cyclobutylpiperazine-1-carboxylate:hydrochloric acid ratio of about 1:1 is reached; and (e) isolate the solids by filtration to obtain the hydrochloride salt of 1-(1-methyl-6-oxo-1,6-dihydropyridazin-3-yl)piperidin-4-yl 4-cyclobutylpiperazine-1-carboxylate in crystalline form.

BRIEF DESCRIPTION OF THE DRAWINGS

FIG. 2A shows the XRPD pattern for Form A of the citrate salt of 1-(1-methyl-6-oxo-1,6-dihydropyridazin-3-yl)piperidin-4-yl 4-cyclobutylpiperazine-1-carboxylate. The x-axis represents the angle of refraction 2-theta, wherein a scale mark corresponds to 1.0 2-theta and wherein the first scale mark is 3.0 2-theta. The y-axis represents Lin (Counts), wherein a scale mark corresponds to 1 count and wherein the first scale mark is 1 count.

FIG. 3A shows the XRPD pattern for Form A of the hydrochloride salt of 1-(1-methyl-6-oxo-1,6-dihydropyridazin-3-yl)piperidin-4-yl 4-cyclobutylpiperazine-1-carboxylate. The x-axis represents the angle of refraction 2-theta, wherein a scale mark corresponds to 1.0 2-theta and wherein the first scale mark is 3.0 2-theta. The y-axis represents Lin (Counts), wherein a scale mark corresponds to 5 counts and wherein the first scale mark is 5 counts.

FIG. 4B shows the XRPD pattern for Form B of the fumarate salt of 1-(1-methyl-6-oxo-1,6-dihydropyridazin-3-yl)piperidin-4-yl 4-cyclobutylpiperazine-1-carboxylate. The x-axis represents the angle of refraction 2-theta, wherein a scale mark corresponds to 2.5 2-theta and wherein the first scale mark is 5.0 2-theta. The y-axis represents Intensity (counts), wherein a scale mark corresponds to 250 counts and wherein the first scale mark is 250 counts.

Figure 1A:
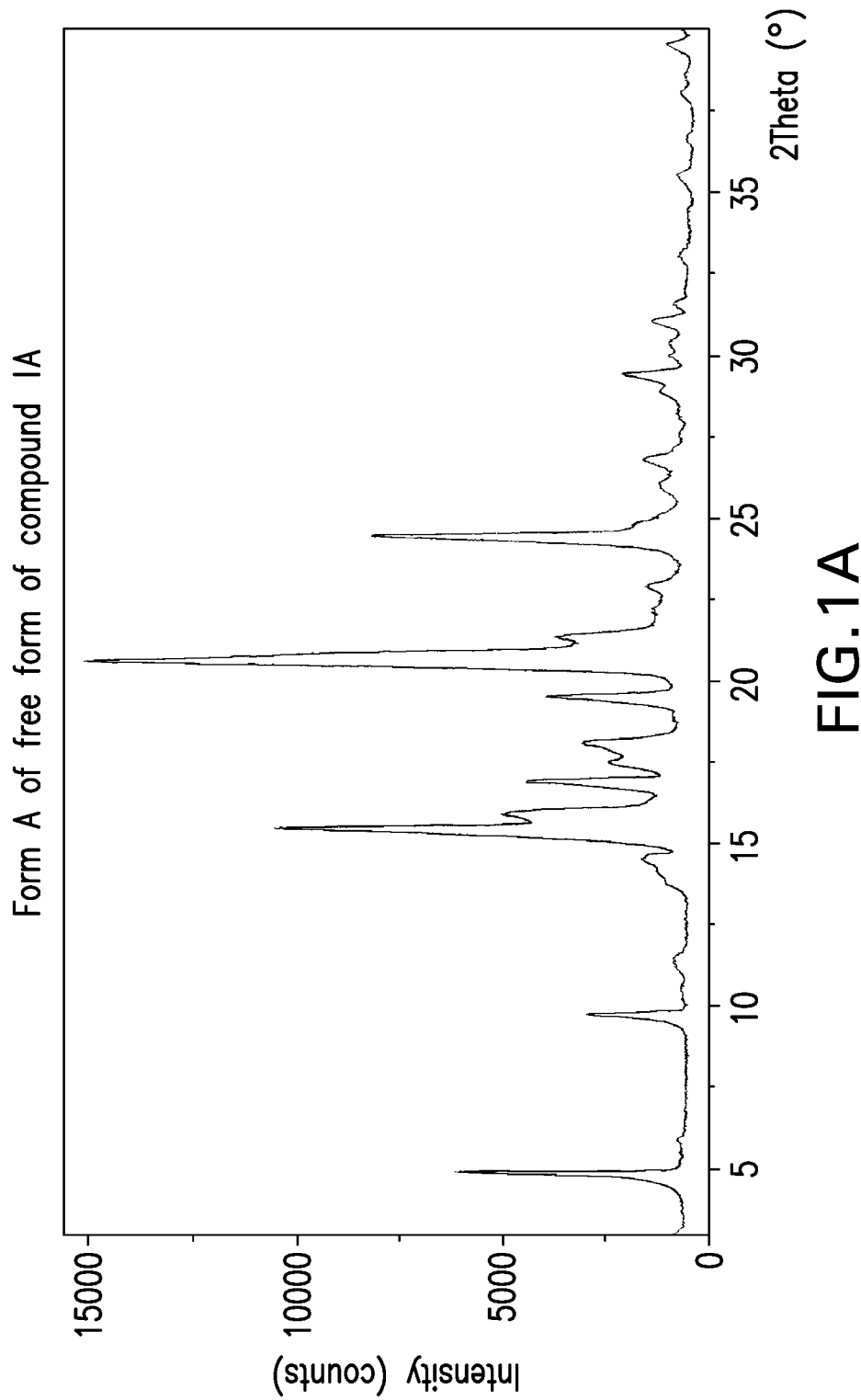
FIG. 1A shows the XRPD pattern for Form A of the free form of 1-(1-methyl-6-oxo-1,6-dihydropyridazin-3-yl)piperidin-4-yl 4-cyclobutylpiperazine-1-carboxylate. The x-axis represents the angle of refraction 2-theta, wherein a scale mark corresponds to 2.5 2-theta and wherein the first scale mark is 5.0 2-theta. The y-axis represents Intensity (counts), wherein a scale mark corresponds to 2500 counts and wherein the first scale mark is 2500 counts.
Figure 1B:
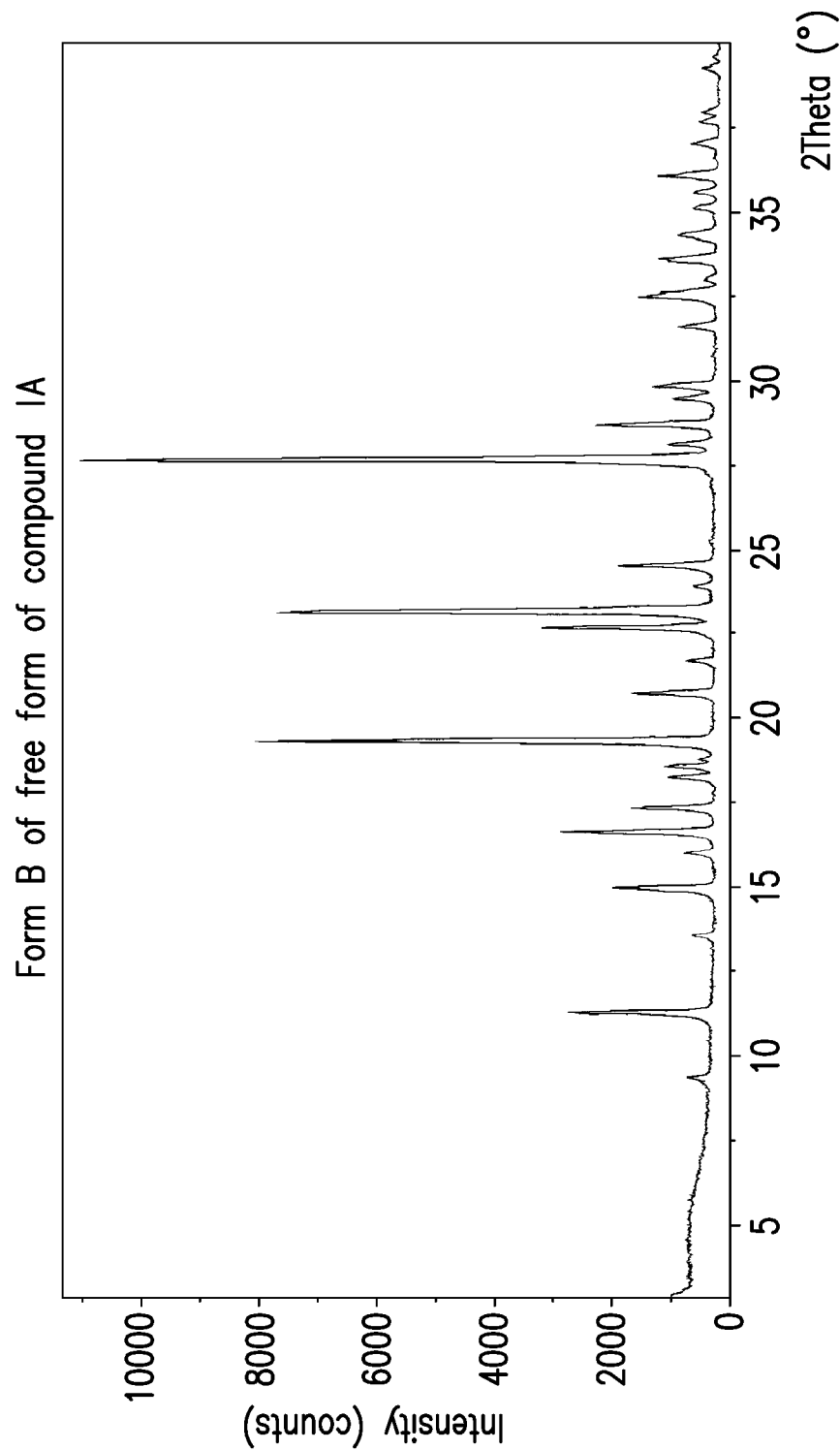
FIG. 1B shows the XRPD pattern for Form B of the free form of 1-(1-methyl-6-oxo-1,6-dihydropyridazin-3-yl)piperidin-4-yl 4-cyclobutylpiperazine-1-carboxylate. The x-axis represents the angle of refraction 2-theta, wherein a scale mark corresponds to 2.5 2-theta and wherein the first scale mark is 5.0 2-theta. The y-axis represents Intensity (counts), wherein a scale mark corresponds to 1000 counts and wherein the first scale mark is 1000 counts.
Figure 2B:
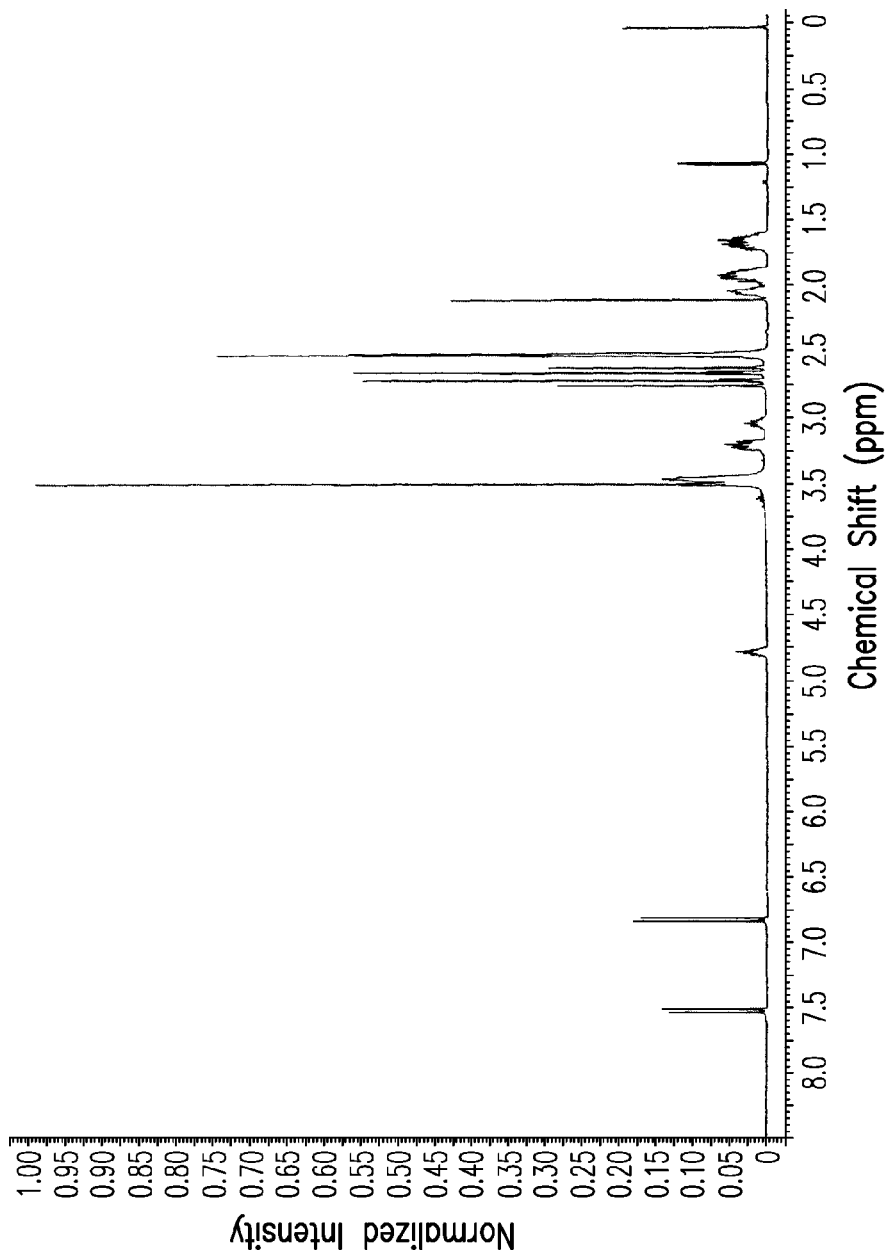
FIG. 2B shows the proton-NMR spectrum for Form A of the citrate salt of 1-(1-methyl-6-oxo-1,6-dihydropyridazin-3-yl)piperidin-4-yl 4-cyclobutylpiperazine-1-carboxylate The x-axis represents the Chemical Shift (ppm), wherein a scale mark corresponds to 0.05 ppm and wherein the first scale mark is 8.45 ppm. The y-axis represents Normalized Intensity, wherein a scale mark corresponds to 0.005 and wherein the first scale mark is −0.02.
Figure 2C:
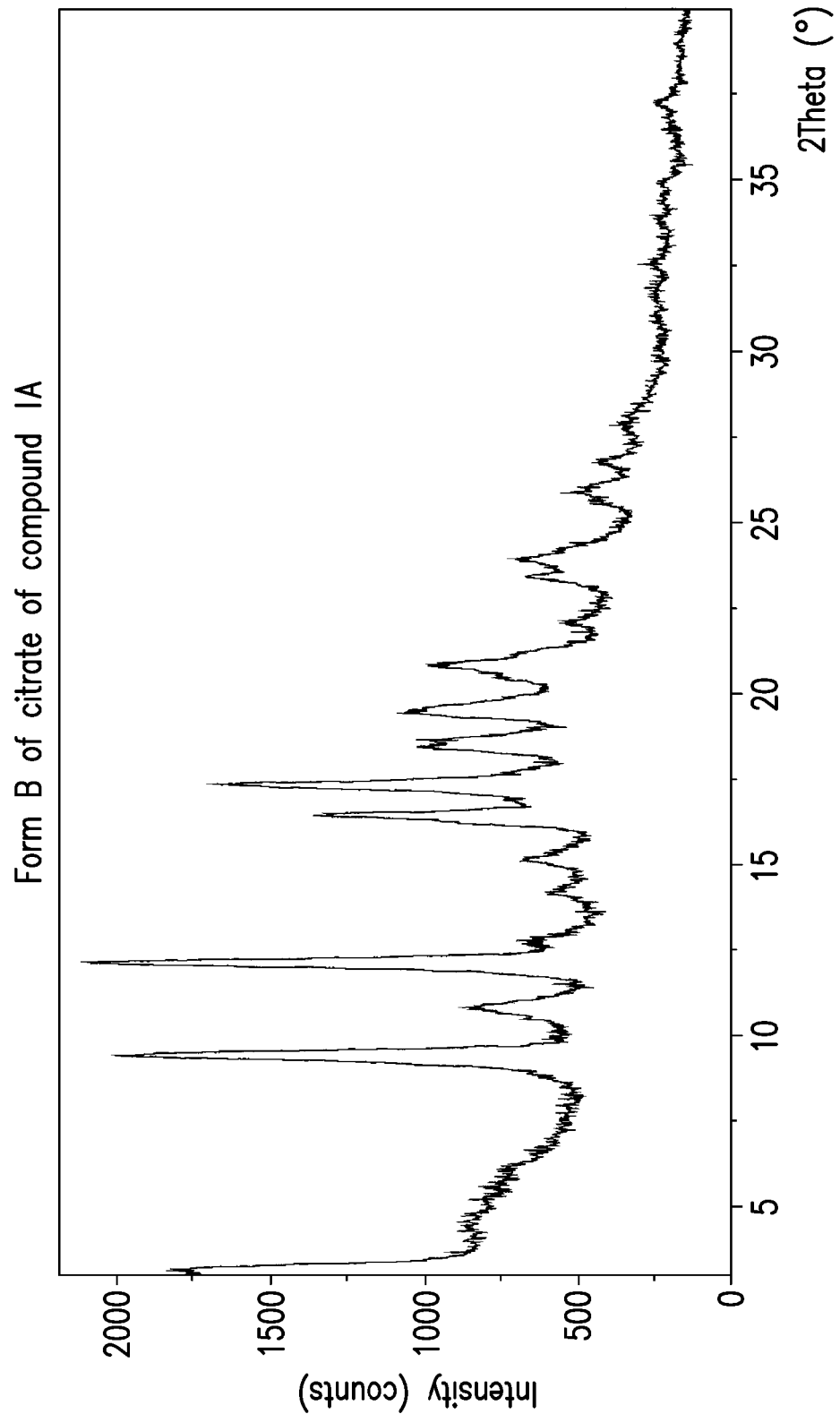
FIG. 2C shows the XRPD pattern for Form B of the citrate salt of 1-(1-methyl-6-oxo-1,6-dihydropyridazin-3-yl)piperidin-4-yl 4-cyclobutylpiperazine-1-carboxylate. The x-axis represents the angle of refraction 2-theta, wherein a scale mark corresponds to 2.5 2-theta and wherein the first scale mark is 5.0 2-theta. The y-axis represents Intensity (counts), wherein a scale mark corresponds to 250 counts and wherein the first scale mark is 250 counts.
Figure 3B:
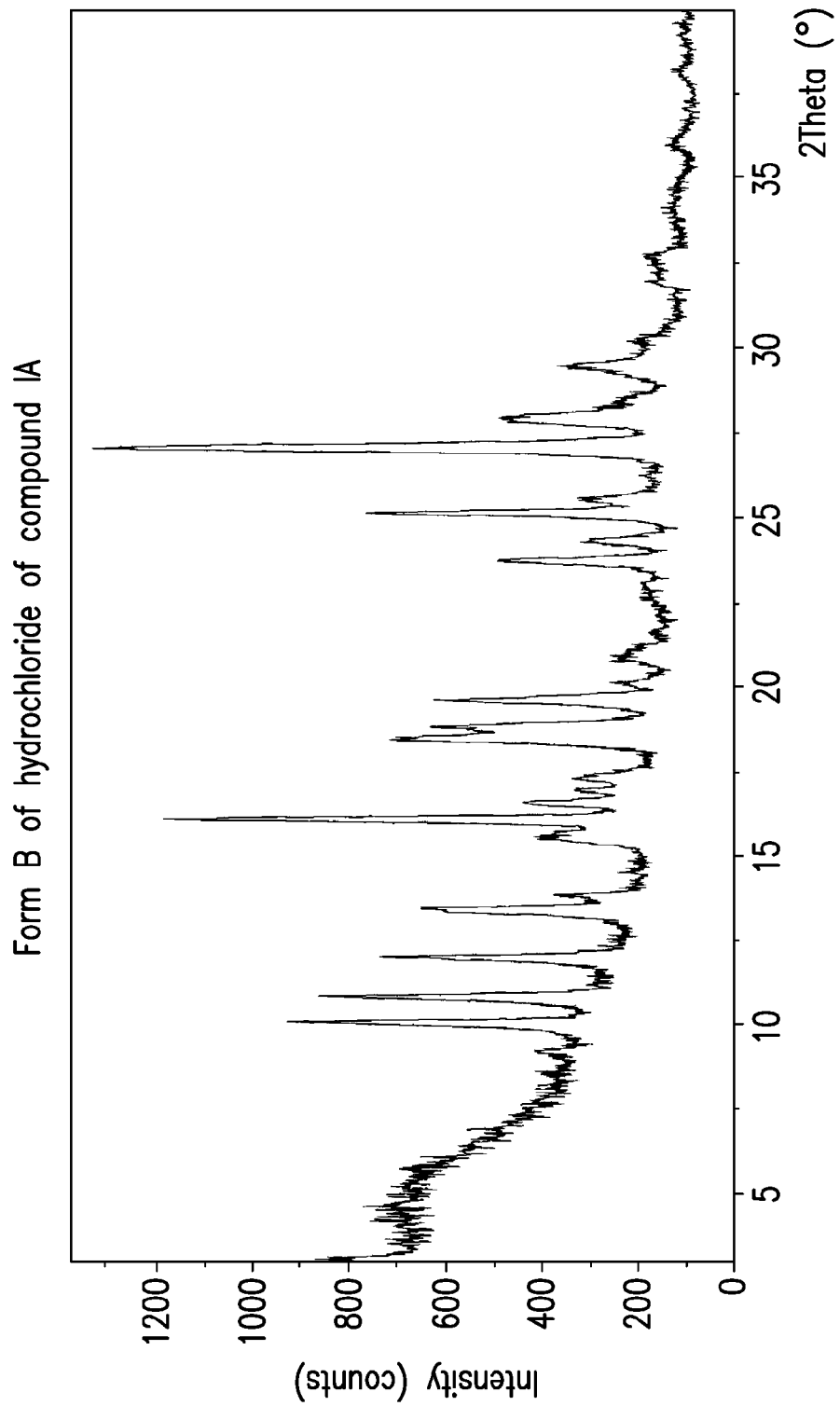
FIG. 3B shows the XRPD pattern for Form B of the hydrochloride salt of 1-(1-methyl-6-oxo-1,6-dihydropyridazin-3-yl)piperidin-4-yl 4-cyclobutylpiperazine-1-carboxylate. The x-axis represents the angle of refraction 2-theta, wherein a scale mark corresponds to 2.5 2-theta and wherein the first scale mark is 5.0 2-theta. The y-axis represents Intensity (counts), wherein a scale mark corresponds to 100 counts and wherein the first scale mark is 100 counts.
Figure 4A:
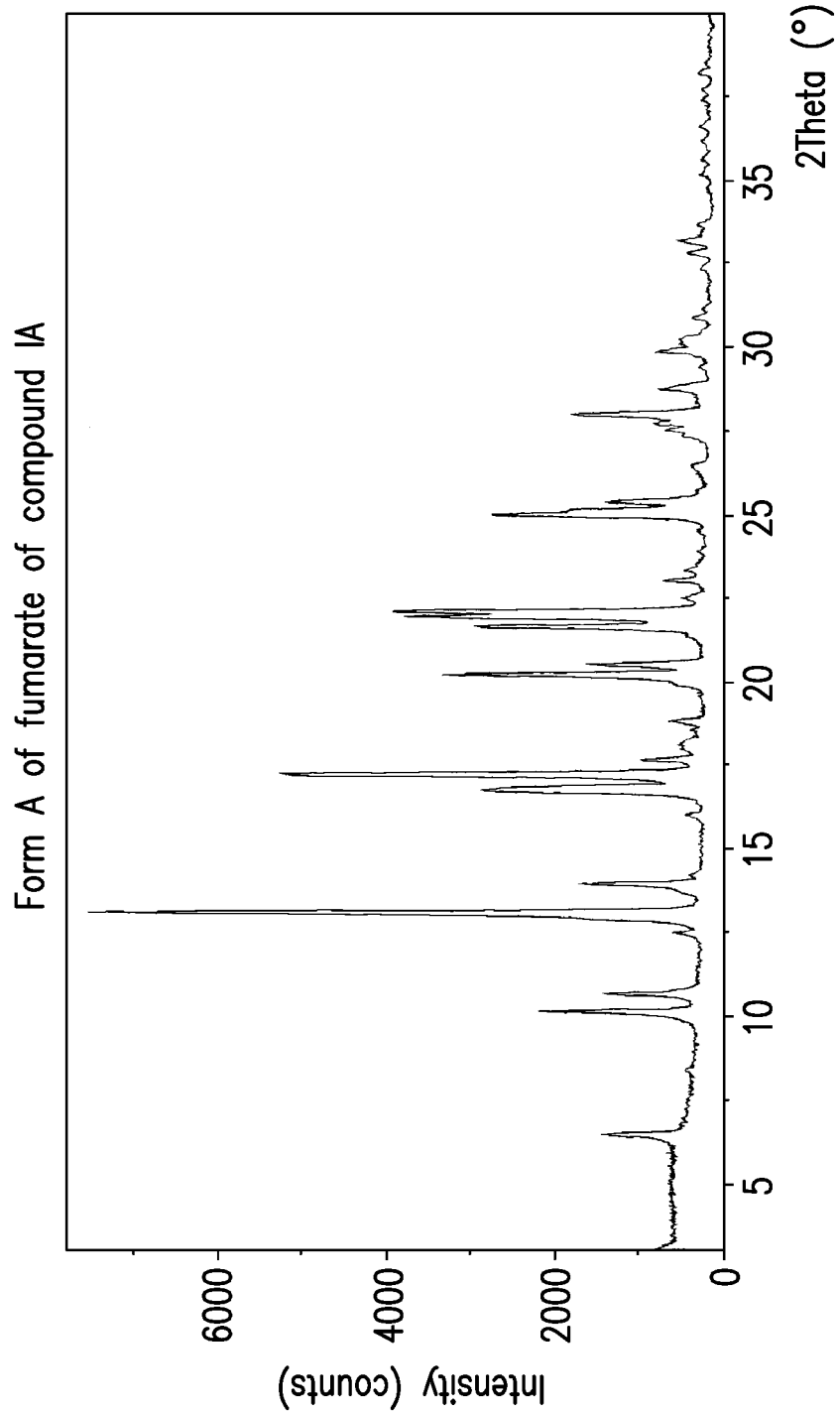
FIG. 4A shows the XRPD pattern for Form A of the fumarate salt of 1-(1-methyl-6-oxo-1,6-dihydropyridazin-3-yl)piperidin-4-yl 4-cyclobutylpiperazine-1-carboxylate. The x-axis represents the angle of refraction 2-theta, wherein a scale mark corresponds to 2.5 2-theta and wherein the first scale mark is 5.0 2-theta. The y-axis represents Intensity (counts), wherein a scale mark corresponds to 1000 counts and wherein the first scale mark is 1000 counts.

The invention claimed is:

1. A method of treating a disorder mediated through antagonism or inverse agonism of the H3 receptor wherein the disorder is a disorder of sleep and wakefulness with excessive daytime sleepiness or a disorder associated with increased fatigue or hypersomnolence comprising administration of 1-(6-oxo-1,6-dihydropyridazin-3-yl)piperidin-4-yl 4-cyclobutylpiperazine-1-carboxylate having the following formula

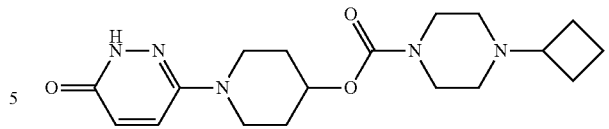

or a pharmaceutically acceptable salt thereof, to a patient in need thereof.

2. The method according to claim 1 where the disorder of sleep and wakefulness with excessive daytime sleepiness is narcolepsy.

3. The method according to claim 1 where the disorder of sleep and wakefulness with excessive daytime sleepiness is obstructive sleep apnea syndrome.

4. The method according to claim 1 where the disorder associated with increased fatigue or hypersomnolence is fatigue associated with Parkinson's disease.

5. The method according to claim 1 where the disorder associated with increased fatigue or hypersomnolence is fatigue associated with multiple sclerosis.

6. The method according to claim 1 where in the disorder associated with increased fatigue or hypersomnolence is fatigue associated shift-work.

7. A method of treating a disorder mediated through antagonism or inverse agonism of the H3 receptor wherein the disorder is a disorder of sleep and wakefulness with excessive daytime sleepiness or a disorder associated with increased fatigue or hypersomnolence comprising administration of 1-(1-methyl-6-oxo-1,6-dihydropyridazin-3-yl)piperidin-4-yl 4-isopropylpiperazine-1-carboxylate having the following formula

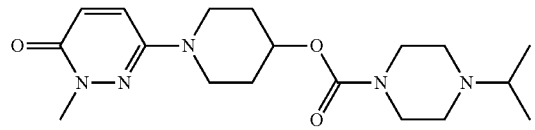

or a pharmaceutically acceptable salt thereof, to a patient in need thereof.

8. The method according to claim 7 where the disorder of sleep and wakefulness with excessive daytime sleepiness is narcolepsy.

9. The method according to claim 7 where the disorder of sleep and wakefulness with excessive daytime sleepiness is obstructive sleep apnea syndrome.

10. The method according to claim 7 where the disorder associated with increased fatigue or hypersomnolence is fatigue associated with Parkinson's disease.

11. The method according to claim 7 where the disorder associated with increased fatigue or hypersomnolence is fatigue associated with multiple sclerosis.

12. The method according to claim 7 where in the disorder associated with increased fatigue or hypersomnolence is fatigue associated shift-work.

13. A method of treating a disorder mediated through antagonism or inverse agonism of the H3 receptor wherein the disorder is a disorder of sleep and wakefulness with excessive daytime sleepiness or a disorder associated with increased fatigue or hypersomnolence comprising administration of 1-(6-oxo-1,6-dihydropyridazin-3-yl)piperidin-4-yl 4-isopropylpiperazine-1-carboxylate having the following formula

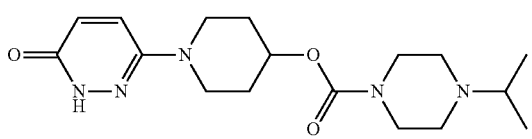 [SMILES: CC(C)N1CCN(C(=O)OC2CCN(c3ccc(=O)[nH]n3)CC2)CC1]

or a pharmaceutically acceptable salt thereof, to a patient in need thereof.

14. The method according to claim 13 where the disorder of sleep and wakefulness with excessive daytime sleepiness is narcolepsy.

15. The method according to claim 13 where the disorder of sleep and wakefulness with excessive daytime sleepiness is obstructive sleep apnea syndrome.

16. The method according to claim 13 where the disorder associated with increased fatigue or hypersomnolence is fatigue associated with Parkinson's disease.

17. The method according to claim 13 where the disorder associated with increased fatigue or hypersomnolence is fatigue associated with multiple sclerosis.

18. The method according to claim 13 where in the disorder associated with increased fatigue or hypersomnolence is fatigue associated shift-work.

19. A method of treating a disorder mediated through antagonism or inverse agonism of the H3 receptor wherein the disorder is a disorder of sleep and wakefulness with excessive daytime sleepiness or a disorder associated with increased fatigue or hypersomnolence comprising administration of 1-(1-methyl-6-oxo-1,6-dihydropyridazin-3-yl)piperidin-4-yl 4-cyclobutylpiperazine-1-carboxylate having the following formula

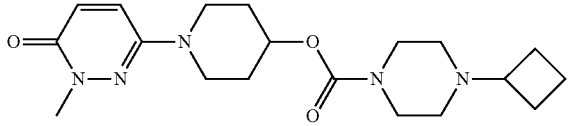 [SMILES: Cn1nc(N2CCC(OC(=O)N3CCN(C4CCC4)CC3)CC2)ccc1=O]

or a pharmaceutically acceptable salt thereof, to a patient in need thereof.

20. The method according to claim 19 where the disorder of sleep and wakefulness with excessive daytime sleepiness is narcolepsy.

21. The method according to claim 19 where the disorder of sleep and wakefulness with excessive daytime sleepiness is obstructive sleep apnea syndrome.

22. The method according to claim 19 where the disorder associated with increased fatigue or hypersomnolence is fatigue associated with Parkinson's disease.

23. The method according to claim 19 where the disorder associated with increased fatigue or hypersomnolence is fatigue associated with multiple sclerosis.

24. The method according to claim 19 where in the disorder associated with increased fatigue or hypersomnolence is fatigue associated shift-work.

\* \* \* \* \*